United States Patent
Pan et al.

(10) Patent No.: US 12,139,654 B1
(45) Date of Patent: Nov. 12, 2024

(54) PRASEODYMIUM-DOPED UPCONVERSION PHOSPHOR

(71) Applicant: KING FAHD UNIVERSITY OF PETROLEUM AND MINERALS, Dhahran (SA)

(72) Inventors: Zhengwei Pan, Dhahran (SA); Yafei Chen, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 18/756,677

(22) Filed: Jun. 27, 2024

Related U.S. Application Data

(60) Provisional application No. 63/565,317, filed on Mar. 14, 2024.

(51) Int. Cl.
| | |
|---|---|
| *C09K 11/77* | (2006.01) |
| *A61L 2/08* | (2006.01) |
| *C01B 33/32* | (2006.01) |
| *C02F 1/32* | (2023.01) |
| *C02F 1/72* | (2023.01) |
| *C09D 5/22* | (2006.01) |

(Continued)

(52) U.S. Cl.
CPC ........ *C09K 11/77742* (2021.01); *A61L 2/088* (2013.01); *C01B 33/32* (2013.01); *C02F 1/32* (2013.01); *C02F 1/725* (2013.01); *C09D 5/22* (2013.01); *C09D 7/61* (2018.01); *C09D 7/69* (2018.01); *C01P 2002/54* (2013.01); *C01P 2002/72* (2013.01); *C01P 2004/61* (2013.01); *C01P 2006/60* (2013.01); *C02F 2303/04* (2013.01); *C02F 2305/10* (2013.01); *C08K 2003/343* (2013.01); *C08K 2201/005* (2013.01)

(58) Field of Classification Search
CPC .. A61L 2/088; C09D 5/22; C09D 7/61; C09D 7/69; C01B 33/32; C08K 2003/343; C08K 2201/005; C09K 11/77742; C01P 2002/54; C01P 2002/72; C01P 2004/61; C01P 2006/60; C02F 1/32; C02F 1/725; C02F 2303/04; C02F 2305/10
See application file for complete search history.

(56) References Cited

U.S. PATENT DOCUMENTS 10,995,102 B2  5/2021  Wang et al.

FOREIGN PATENT DOCUMENTS

| CN | 103296120 A | 9/2013 |
|---|---|---|
| CN | 104927864 A | 9/2015 |

(Continued)

OTHER PUBLICATIONS

Hui et al. ; Luminescent properties of Pr3+ doped LiYF4 glass ceramics for white light-emitting diodes ; Acta Photonica Sinica, vol. 47, Issue 9, Sep. 2018 ; 9 Pages.

(Continued)

*Primary Examiner* — John Kim
(74) *Attorney, Agent, or Firm* — Oblon, McClelland, Maier & Neustadt, L.L.P.

(57) ABSTRACT

An upconversion phosphor having a formula of Li—R—Si—O—F:xPr$^{3+}$, where R is yttrium (Y) or lutetium (Lu). The value of x is 0.001 to 5 and represents a mole percentage (%) based on the total number of moles of all elements in the upconversion phosphor. Following excitation with sunlight, the upconversion phosphor emits light with a wavelength in the range of 250 nanometers (nm) to 350 nm.

19 Claims, 25 Drawing Sheets

(51) Int. Cl.
  *C09D 7/40*  (2018.01)
  *C09D 7/61*  (2018.01)
  *C08K 3/34*  (2006.01)

(56) References Cited

FOREIGN PATENT DOCUMENTS

| CN | 105018088 A | 11/2015 |
|---|---|---|
| CN | 107365583 A | 11/2017 |

OTHER PUBLICATIONS

Yan et al. ; A considerable improvement of long-persistent luminescence in LiLuSiO4: Pr3+ phosphors by Sm3+ co-doping for optical tagging applications ; Journal of Materials Chemistry C, vol. 10, Issue 45 ; 2022 ; Abstract Only ; 4 Pages.

Cates et al. ; Converting Visible Light into UVC: Microbial Inactivation by Pr3+ Activated Upconversion Materials ; Environmental Science & Technology, 45 ; 2011 ; 7 Pages.

Hu et al. ; Visible-to-ultraviolet upconversion in Pr3+:Y2SiO5 crystals ; Chemical Physics 325 ; 2006 ; 4 Pages.

Cates et al. ; Balancing intermediate state decay rates for efficient Pr3+ visible-to-UVC upconversion: the case of b-Y2Si2O7:Pr3+ ; RSC Advances, 6 ; Feb. 20, 2016 ; 6 Pages.

Yin et al. ; Pr3+ doped Li2SrSiO4: an efficient visible-ultraviolet C up-conversion phosphor ; Ceramics International 47 ; Oct. 14, 2020; 6 Pages.

Cates et al. ; Upconversion under polychromatic excitation: Y2SiO5: Pr3+, Li+ converts violet, cyan, green, and yellow light into UVC; Optical Materials 35 ; Jul. 17, 2013 ; 5 Pages.

Cates et al. ; Visible-to-UVC upconversion efficiency and mechanisms of Lu7O6F9: Pr3þ and Y2SiO5:Pr3þ ceramics ; Journal of Luminescence 160 ; Dec. 17, 2014 ; 8 Pages.

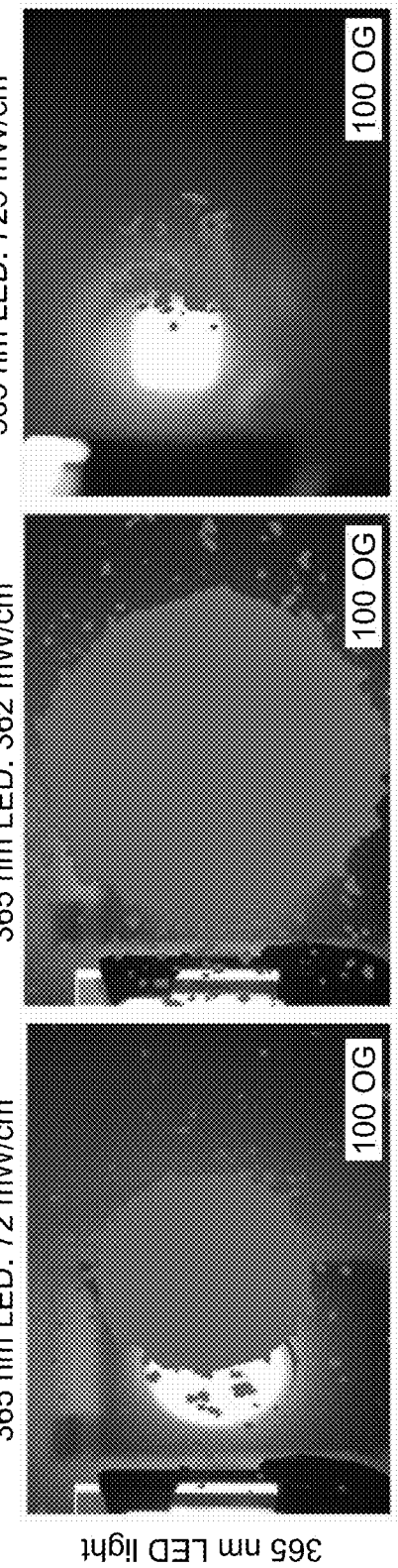

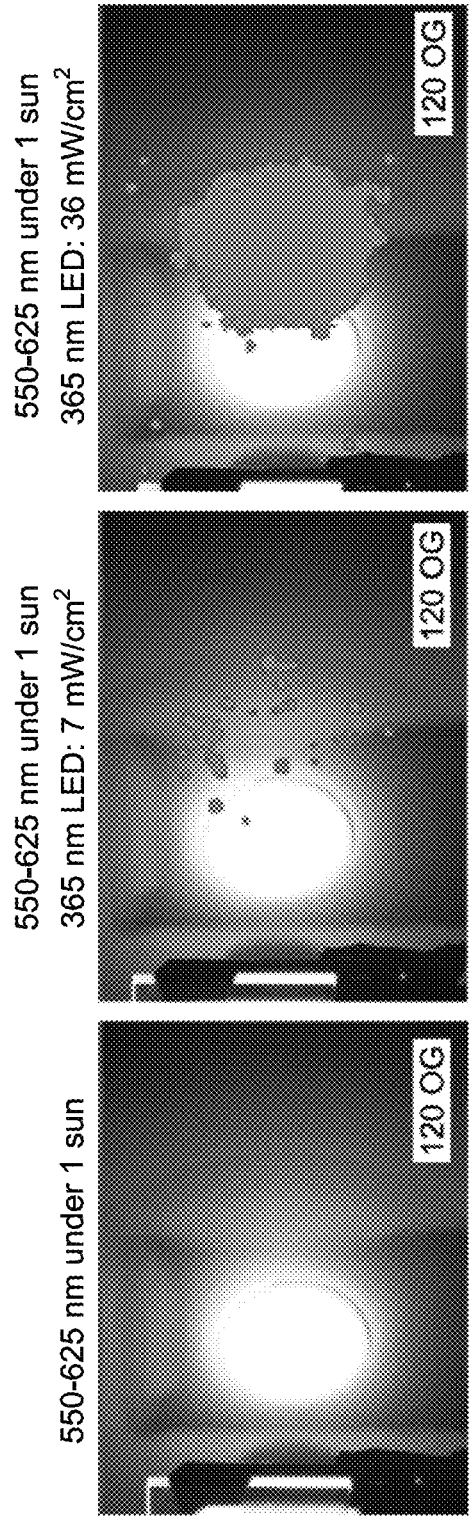
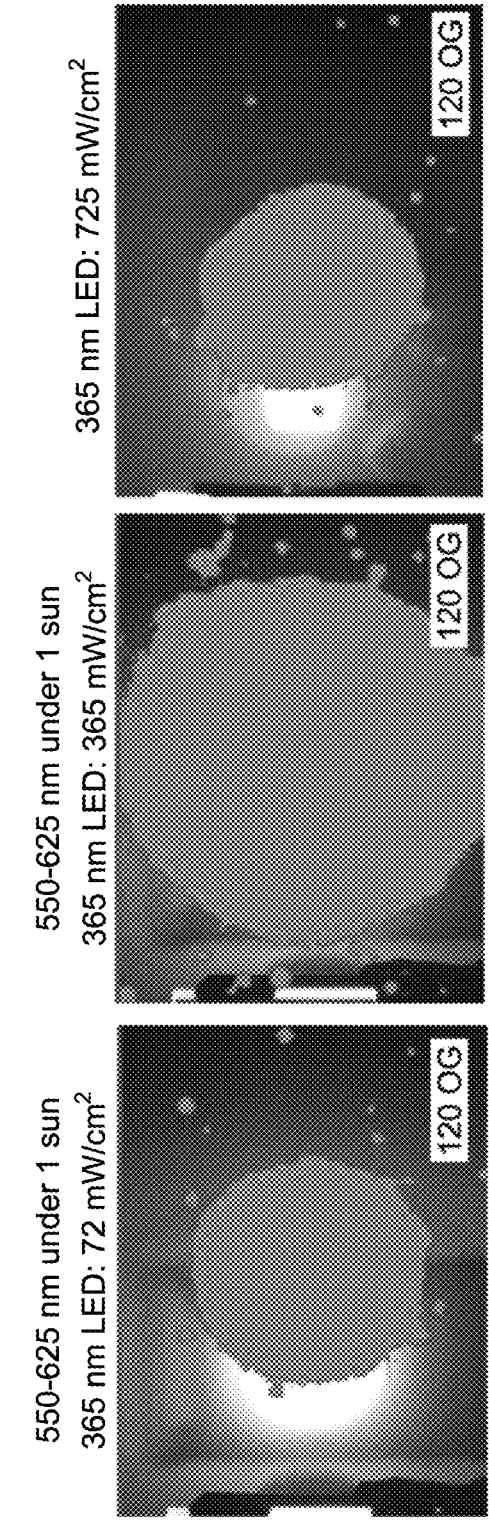
FIG. 5G  FIG. 5H  FIG. 5I  
FIG. 5J  FIG. 5K  FIG. 5L

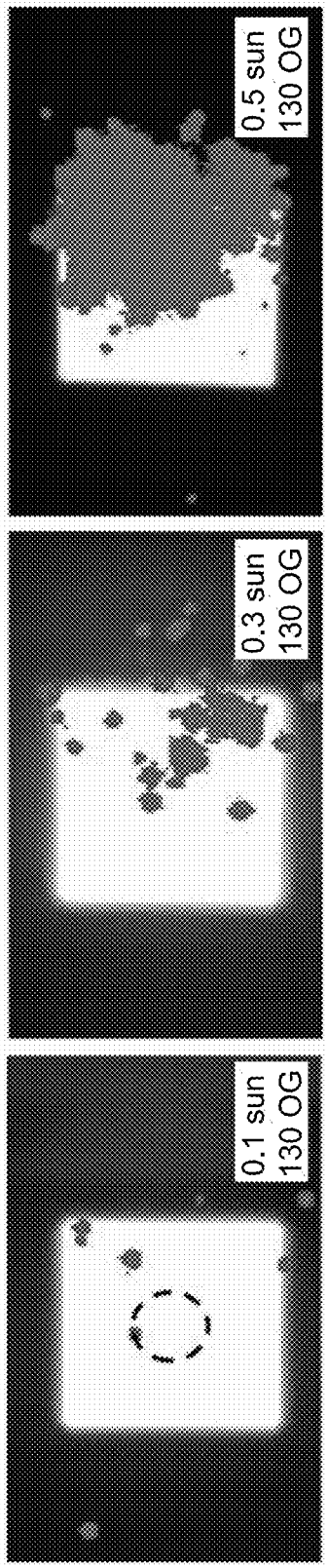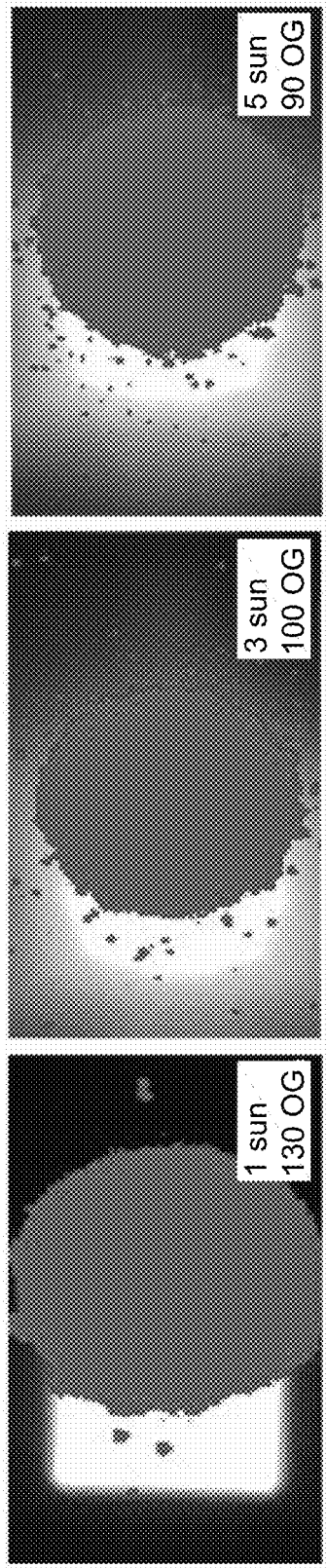

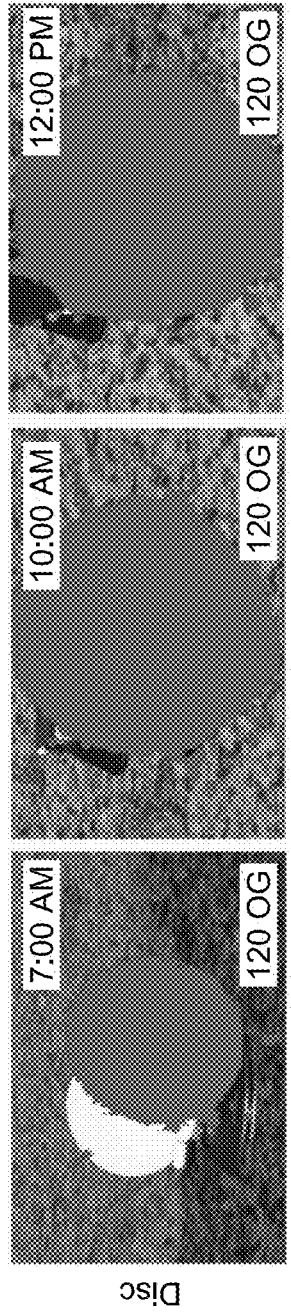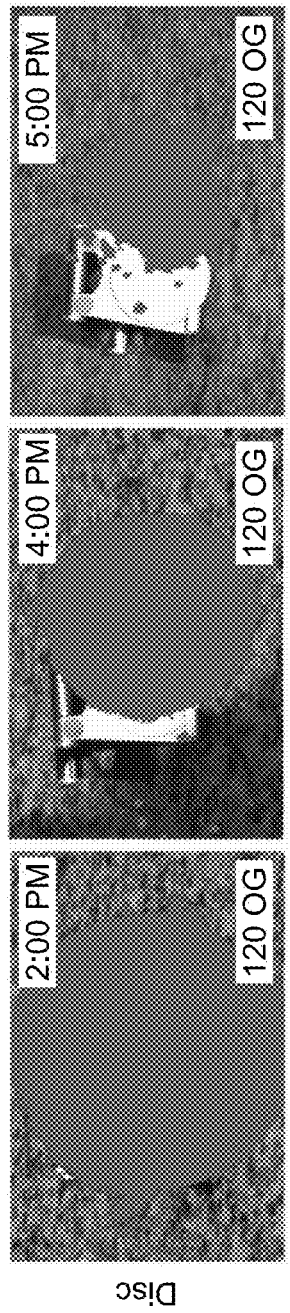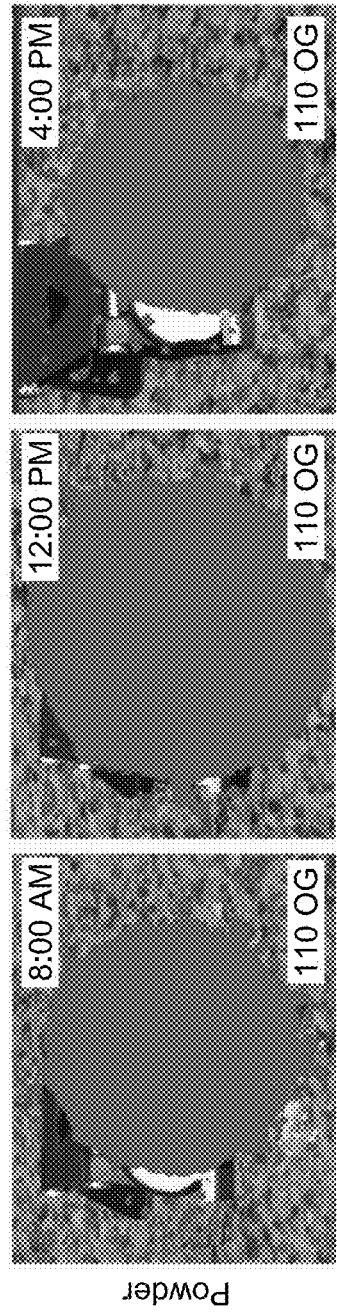

PRASEODYMIUM-DOPED UPCONVERSION PHOSPHOR

CROSS REFERENCE TO RELATED APPLICATIONS

This application is related to provisional application 63/565,317, filed on Mar. 14, 2024, incorporated herein by reference.

STATEMENT OF ACKNOWLEDGEMENT

Support provided by the King Fahd University of Petroleum and Minerals (KFUPM) is gratefully acknowledged.

BACKGROUND

Technical Field

The present disclosure is directed towards an upconversion (UC) phosphor, more particularly directed towards a praseodymium doped UC phosphor.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

The wavelength range of ultraviolet-C (UVC) radiation is 200 nanometers (nm) to 280 nm. UVC is widely used for disinfection, as UVC has a spectral overlap with the germicidal effectiveness curve, which is around 220 nm to 280 nm. The germicidal effectiveness is highest at 265 nm. UVC may sterilize water, air, food, surfaces, and consumables in municipal water plants, hospitals, food industries, public areas, transportation facilities, and residential and commercial spaces.

Another use of UVC radiation is photocatalysis. In photocatalysis, UVC radiation excites for example titanium oxide ($TiO_2$) nanoparticles to produce highly reactive oxygen species, such as hydroxyl radicals and superoxide radical anions. These highly reactive oxygen species may degrade or decompose the species absorbed on the $TiO_2$ nanoparticles. The absorbed species include but are not limited to particulate matter, volatile organic compounds, non-volatile biological agents such as bacteria, molds, viruses, and inorganic gaseous pollutants such as nitrogen oxides ($NO_x$) and sulfur oxides ($SO_x$). As a result, UVC-induced $TiO_2$ photocatalysis is increasingly researched and used for environmental remediation, such as industrial wastewater treatment and indoor air purification. Further, UVC-induced $TiO_2$ photocatalytic oxidation is also researched to produce energy, such as hydrogen production by water splitting and carbon dioxide ($CO_2$) conversion to hydrocarbon fuels.

An appropriate UVC radiation source is required for disinfection and photocatalysis. Due to the absorption of radiation by the Earth's atmosphere and ozone layer, UVC radiation from the Sun does not reach the Earth's surface. This is why the UVC spectral domain is called "solar-blind". Low-pressure mercury discharge lamps emitting 254 nm are used as UVC radiation sources. Although mercury lamps are bright and moderately efficient, they are fragile and contain toxic mercury. Therefore, a need arises to find an alternative to mercury lamps as UVC radiation sources. One alternative to mercury-based UVC radiation sources is UVC light-emitting diodes (LEDs) based on aluminum gallium nitride (AlGaN) semiconductors. However, AlGaN-based UVC LEDs are inefficient, and thermal management of AlGaN-based UVC LEDs is not economical.

The artificial UVC radiation sources, including the mercury UVC lamps and AlGaN UVC LEDs, run on electricity. Further, due to small sizes and limited powers, UVC lamps and LEDs are suitable only for indoor environments and other confined spaces such as hospitals and municipal water plants. However, UVC lamps and LEDs as sources of UVC radiation for applications in vast outdoor environments are impractical and uneconomical. Hence, sunlight may be considered as an ideal energy source to power a UVC radiation source for outdoor environments and energy applications. Theoretically, this may be achieved by a phosphor that may upconvert the low-energy, low-power-intensity, and broad-band solar photons into higher-energy, solar-blind UVC photons. Such phosphor is known as an upconversion (UC) phosphor.

Praseodymium ($Pr^{3+}$) doped UC phosphors are used in developing sunlight to UVC or visible light to UVC because the energy level structure of $Pr^{3+}$ allows emitting one UVC photon at around 265 nm to 275 nm after sequentially absorbing two lower-energy visible photons in a two-step UC process. Further, a plurality of $Pr^{3+}$-doped silicate-based visible to UVC UC phosphors exists, such as $Pr^{3+}$-doped yttrium orthosilicate ($Y_2SiO_5:Pr^{3+}$), $Pr^{3+}$-doped lutetium oxyfluoride ($Lu_7O_6F_9:Pr^{3+}$) $Pr^{3+}$-doped yttrium silicate ($Y_2Si_2O_7:Pr^{3+}$), and $Pr^{3+}$-doped lithium strontium silicate ($Li_2SrSiO_4:Pr^{3+}$). However, blue lasers of power-intensity 1 watt per square centimeter ($W/cm^2$) to 1000 $W/cm^2$ and wavelength of 440 nm to 480 nm are required to excite the phosphors. In applications of visible to UVC UC phosphors, such as antimicrobial surface and environmental technologies, the intended excitation sources are the visible light sources, such as sunlight and LED light, which have intensities lower than 100 milliwatts per square centimeter ($mW/cm^2$). The total intensity of solar visible light is around 44 $mW/cm^2$. Due to low or undetectable UVC luminescence, it is impractical to use such UC phosphors in environmental applications, such as solar photocatalysis.

Each of the aforementioned methods suffers from one or more drawbacks hindering their adoption. Accordingly, it is one object of the present disclosure to provide methods and systems for a visible to UVC UC process using a low-power-intensity visible light that may circumvent the aforementioned drawbacks and limitations of traditional methods.

SUMMARY

In an exemplary embodiment, an upconversion phosphor is described. The upconversion phosphor has the formula Li—R—Si—O—F:$xPr^{3+}$, where R is yttrium (Y) or lutetium (Lu) and the value of x is 0.001 to 5 and represents mole percentage (%) based on the total number of moles of all elements in the upconversion phosphor. Following excitation with sunlight, the upconversion phosphor emits light having a wavelength in a range of 250 nanometers (nm) to 350 nm.

In some embodiments, when excited with sunlight, the upconversion nanophosphor emits light having a maximum peak wavelength in a range of 255 nm to 270 nm.

In some embodiments, the upconversion phosphor has a formula of $(LiYSiO_4)(LiF)_n:xPr^{3+}$, where the value of n is 0.1 to 3.

In some embodiments, the upconversion phosphor has a formula of $(Y_2SiO_5)(LiF)_n:xPr^{3+}$, where the value of n is 0.1 to 3.

In some embodiments, the upconversion phosphor has a formula of $(LiLuSiO_4)(LiF)_n:xPr^{3+}$, where the value of n is 0.1 to 3.

In some embodiments, the upconversion phosphor has a formula of $(Lu_2SiO_5)(LiF)_n:xPr^{3+}$, where the value of n is 0.1 to 3.

In some embodiments, the formula of the upconversion phosphor is selected from the group consisting of $LiYSiO_{3.5}F:xPr^{3+}$, $Li_{1.6}YSiO_{3.5}F_{1.6}:xPr^{3+}$, $Li_{2.5}YSiO_4F_{1.5}:xPr^{3+}$, $Li_2Y_2SiO_5F_2:xPr^{3+}$, $LiY_2Si_{1.5}O_{4.5}F_4:xPr^{3+}$, $Li_{1.5}Y_2SiO_5F_{1.5}:xPr^{3+}$, and $LiLu_2SiO_5F:xPr^{3+}$.

In some embodiments, the upconversion phosphor has at least one crystal phase selected from the group consisting of $LiY_3(SiO_4)_3F_2$ and $\beta-Y_2Si_2O_7$.

In some embodiments, the upconversion phosphor does not include $Pr^{4+}$.

In some embodiments, the upconversion phosphor has a powder particle size of 5 micrometers (μm) to 20 μm.

In another exemplary embodiment, a paint is described. The paint includes the upconversion phosphor and a fluoropolymer or silicone.

In yet another exemplary embodiment, a method of upconverting light is described. The method includes irradiating the upconversion phosphor with the light and upon irradiating, the upconversion phosphor converts the light to a shorter wavelength light.

In some embodiments, the light is selected from a broadband light source from 300 nm to 625 nm, selected from a group consisting of natural sunlight, simulated sunlight, or a mix of LED light.

In some embodiments, the light has a power density of 0.1 milliwatts per square centimeter ($mW/cm^2$) to 1000 $mW/cm^2$.

In some embodiments, the shorter wavelength light has a wavelength in a range of 250 nm to 350 nm.

In some embodiments, the shorter wavelength light has a maximum peak wavelength in a range of 255 nm to 270 nm.

In some embodiments, the upconversion phosphor has a formula selected from the group including $LiYSiO_{3.5}F:xPr^{3+}$, $Li_{1.6}YSiO_{3.5}F_{1.6}:xPr^{3+}$, $Li_{2.5}YSiO_4F_{1.5}:xPr^{3+}$, $Li_2Y_2SiO_5F_2:xPr^{3+}$, $LiY_2Si_{1.5}O_{4.5}F_4:xPr^{3+}$, $Li_{1.5}Y_2SiO_5F_{1.5}:xPr^{3+}$, and $LiLu_2SiO_5F:xPr^{3+}$.

In some embodiments, the upconversion phosphor is dispersed in water.

In some embodiments, the shorter wavelength light is capable of disinfecting a surface or a solution.

The foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 5A is an image showing upconversion UVC emission of a $LiYSiO_{3.5}F:0.005Pr^{3+}$ phosphor disk under the excitation of 440 nm to 500 nm solar band under 1 sun, according to certain embodiments.

FIG. 5B is an image showing upconversion UVC emission of a $LiYSiO_{3.5}F:0.005Pr^{3+}$ phosphor disk under the excitation of 440 nm to 500 nm solar band combined with a 365 nm LED of 7 $mW/cm^2$ intensity, according to certain embodiments.

FIG. 5C is an image showing upconversion UVC emission of a $LiYSiO_{3.5}F:0.005Pr^{3+}$ phosphor disk under the excitation of 440 nm to 500 nm solar band combined with a 365 nm LED of 36 $mW/cm^2$ intensity, according to certain embodiments.

FIG. 5D is an image showing upconversion UVC emission of a $LiYSiO_{3.5}F:0.005Pr^{3+}$ phosphor disk under the excitation of 440 nm to 500 nm solar band combined with a 365 nm LED of 72 $mW/cm^2$ intensity, according to certain embodiments.

FIG. 5E is an image showing upconversion UVC emission of a $LiYSiO_{3.5}F:0.005Pr^{3+}$ phosphor disk under the excitation of 440 nm to 500 nm solar band combined with a 365 nm LED of 362 $mW/cm^2$ intensity, according to certain embodiments.

FIG. 5F is an image showing upconversion UVC emission of a $LiYSiO_{3.5}F:0.005Pr^{3+}$ phosphor disk under the excitation of 365 nm LED of 725 $mW/cm^2$ intensity, according to certain embodiments.

FIG. 5G is an image showing upconversion UVC emission of a $LiYSiO_{3.5}F:0.005Pr^{3+}$ phosphor disk under the excitation of 550 nm to 625 nm solar band under 1 sun, according to certain embodiments.

FIG. 5H is an image showing upconversion UVC emission of a $LiYSiO_{3.5}F:0.005Pr^{3+}$ phosphor disk under the excitation of 550 nm to 625 nm solar band combined with 365 nm LED of 7 $mW/cm^2$ intensity, according to certain embodiments.

FIG. 5I is an image showing upconversion UVC emission of a $LiYSiO_{3.5}F:0.005Pr^{3+}$ phosphor disk under the excitation of 550 nm to 625 nm solar band combined with 365 nm LED of 36 $mW/cm^2$ intensity, according to certain embodiments.

FIG. 5J is an image showing upconversion UVC emission of a $LiYSiO_{3.5}F:0.005Pr^{3+}$ phosphor disk under the excitation of 550 nm to 625 nm solar band combined with 365 nm LED of 72 $mW/cm^2$ intensity, according to certain embodiments.

FIG. 5K is an image showing upconversion UVC emission of a LiYSiO$_{3.5}$F:0.005Pr$^{3+}$ phosphor disk under the excitation of 550 nm to 625 nm solar band combined with 365 nm LED of 365 mW/cm$^2$ intensity, according to certain embodiments.

FIG. 5L is an image showing upconversion UVC emission of a LiYSiO$_{3.5}$F:0.005Pr$^{3+}$ phosphor disk under the excitation of 365 nm LED of 725 mW/cm$^2$ intensity, according to certain embodiments.

FIG. 8A is an image of upconversion UVC emission of a LiYSiO$_{3.5}$F:0.005Pr$^{3+}$ phosphor disk under irradiation of 0.1 sun, according to certain embodiments.

FIG. 8B is an image of upconversion UVC emission of a LiYSiO$_{3.5}$F:0.005Pr$^{3+}$ phosphor disk under irradiation of 0.3 suns, according to certain embodiments.

FIG. 8C is an image of upconversion UVC emission of a LiYSiO$_{3.5}$F:0.005Pr$^{3+}$ phosphor disk under irradiation of 0.5 suns, according to certain embodiments.

FIG. 8D is an image of upconversion UVC emission of a LiYSiO$_{3.5}$F:0.005Pr$^{3+}$ phosphor disk under irradiation of 1 sun, according to certain embodiments.

FIG. 8E is an image of upconversion UVC emission of a LiYSiO$_{3.5}$F:0.005Pr$^{3+}$ phosphor disk under irradiation of 3 suns, according to certain embodiments.

FIG. 8F is an image of upconversion UVC emission of a LiYSiO$_{3.5}$F:0.005Pr$^{3+}$ phosphor disk under irradiation of 5 suns, according to certain embodiments.

FIG. 9A is an image of upconversion UVC emission of a LiYSiO$_{3.5}$F:0.005Pr$^{3+}$ phosphor disk under the excitation of natural sunlight at 7:00 am, according to certain embodiments.

FIG. 9B is an image of upconversion UVC emission of a LiYSiO$_{3.5}$F:0.005Pr$^{3+}$ phosphor disk under the excitation of natural sunlight at 10:00 am, according to certain embodiments.

FIG. 9C is an image of upconversion UVC emission of a LiYSiO$_{3.5}$F:0.005Pr$^{3+}$ phosphor disk under the excitation of natural sunlight at noon, according to certain embodiments.

FIG. 9D is an image of upconversion UVC emission of a LiYSiO$_{3.5}$F:0.005Pr$^{3+}$ phosphor disk under the excitation of natural sunlight at 2:00 pm, according to certain embodiments.

FIG. 9E is an image of upconversion UVC emission of a LiYSiO$_{3.5}$F:0.005Pr$^{3+}$ phosphor disk under the excitation of natural sunlight at 4:00 pm, according to certain embodiments.

FIG. 9F is an image of upconversion UVC emission of a LiYSiO$_{3.5}$F:0.005Pr$^{3+}$ phosphor disk under the excitation of natural sunlight at 5:00 pm, according to certain embodiments.

FIG. 9G is an image of upconversion UVC emission of LiYSiO$_{3.5}$F:0.005Pr$^{3+}$ phosphor powder under the excitation of natural sunlight at 8:00 am, according to certain embodiments.

FIG. 9H is an image of upconversion UVC emission of LiYSiO$_{3.5}$F:0.005Pr$^{3+}$ phosphor powder under the excitation of natural sunlight at noon, according to certain embodiments.

FIG. 9I is an image of upconversion UVC emission of LiYSiO$_{3.5}$F:0.005Pr$^{3+}$ phosphor powder under the excitation of natural sunlight at 4:00 pm, according to certain embodiments.

DETAILED DESCRIPTION

Figure 1A:
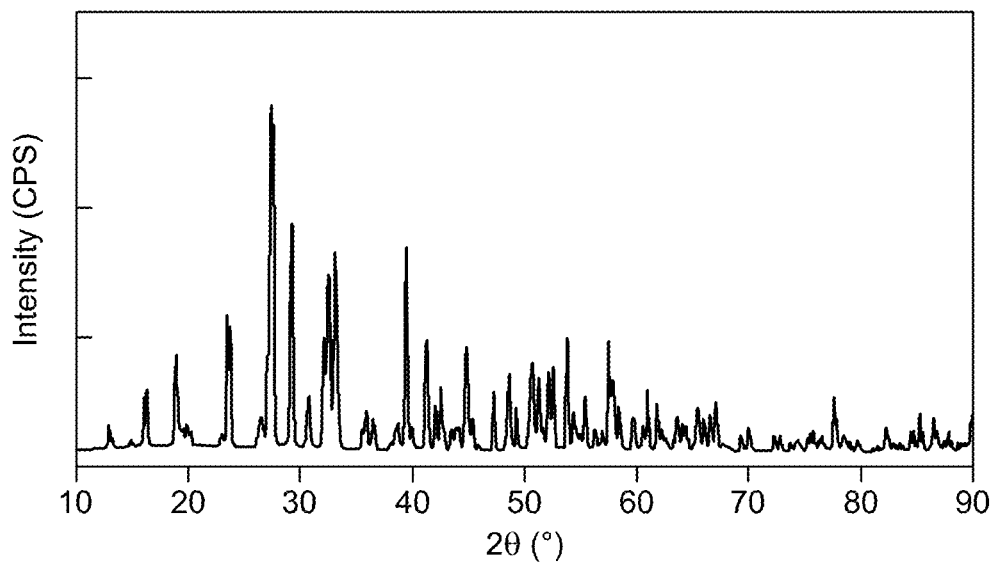
FIG. 1A shows X-ray diffraction (XRD) pattern of a $LiYSiO_{3.5}F:0.005Pr^{3+}$ sample, according to certain embodiments.

When describing the present disclosure, the terms used are to be construed in accordance with the following definitions, unless a context dictates otherwise. Embodiments of the present invention will now be described more fully hereinafter with reference to the accompanying drawings wherever applicable, in that some, but not all embodiments of the disclosure are shown.

In the drawings, reference numerals designate identical or corresponding parts throughout the several views. Further, as used herein, the words "a," "an," and the like generally carry a meaning of "one or more," unless stated otherwise. Furthermore, the terms "approximately," "approximate," "about," and similar terms generally refer to ranges that include the identified value within a margin of 20%, 10%, or preferably 5%, and any values therebetween.

As used herein, "compound" refers to a chemical entity, whether as a solid, liquid, or gas, and whether in a crude mixture or isolated and purified.

As used herein, the term "upconversion phosphors" refers to materials that emit higher-energy photons by absorbing lower-energy photons. Upconversion is achieved by exciting a population in an excited state and then emitting a photon with greater energy than the pump excitation photon.

A weight percent of a component, unless specifically stated to the contrary, is based on the total weight of the formulation or composition in which the component is included. For example, if a particular element or component in a composition or article is said to have 5 wt. %, it is understood that this percentage is in relation to a total compositional percentage of 100%.

Where a numerical limit or range is stated herein, the endpoints are included. Also, all values and subranges within a numerical limit or range are specifically included as if explicitly written out.

The present disclosure is intended to include all isotopes of a given compound or formula, unless otherwise noted, and all hydration states of a given compound or formula, unless otherwise noted or when heating a material.

Aspects of the present disclosure are directed toward sunlight-to-ultraviolet-C (UVC) or visible-to-UVC upconversion phosphors that can be effectively activated by commonly accessible visible light sources such as natural sunlight and light-emitting diodes (LEDs). Phosphors disclosed herein are based on the doping of Pr$^{3+}$ ions and co-doping of Li$^+$/F$^-$ ions into silicate host matrices. The emission wavelengths of the phosphors disclosed herein are in the range of 250-350 nm.

An upconversion phosphor, also referred to as the phosphor, is described. The upconversion phosphor has the formula Li—R—Si—O—F:xPr$^{3+}$. In some embodiments, R is at least one lanthanide selected from the group consisting of lanthanum (La), cerium (Ce), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), and lutetium (Lu). In preferred embodiments, R is yttrium (Y) or lutetium (Lu). Lanthanide dopants are optically active centers and often include a combination of sensitizers and activators. In some embodiments, x is 0.001-5, preferably 0.005-4.95, preferably 0.1-4.9, preferably 0.5-4.5, preferably 1-4, preferably 1.5-3.5, preferably 2-3, and represents mole % based on the total number of moles of all elements in the upconversion phosphor.

In a preferred embodiment, it the process of making the upconversion phosphor provisions are taken to prevent the formation of Pr$^{4+}$, for example by adding graphite powder during a firing to provide a weak reducing environment to prevent the oxidation of Pr$^{3+}$ to Pr$^{4+}$. In some embodiments, the upconversion phosphor does not comprise Pr$^{4+}$. In some embodiments, the upconversion phosphor comprises less than 1 mol % of the $Pr^{4+}$, preferably less than 0.1 mol %, or less than 0.001 mol %.

In an embodiment, the upconversion phosphor has a formula of $(LiYSiO_4)(LiF)_n:xPr^{3+}$. The n is $(LiYSiO_4)(LiF)_n:xPr^{3+}$ is from 0.1-3, preferably 0.25-2.75, preferably 0.5-2.5, preferably 1-2, and preferably 1.25-1.75. In an embodiment, the upconversion phosphor has a formula of $(Y_2SiO_5)(LiF)_n:xPr^{3+}$. The n is $(Y_2SiO_5)(LiF)_n:xPr^{3+}$ is from 0.1-3, preferably 0.25-2.75, preferably 0.5-2.5, preferably 1-2, and preferably 1.25-1.75. In an embodiment, the upconversion phosphor has a formula of $(LiLuSiO_4)(LiF)_n:xPr^{3+}$. The n is $(LiLuSiO_4)(LiF)_n:xPr^{3+}$ is from 0.1-3, preferably 0.25-2.75, preferably 0.5-2.5, preferably 1-2, and preferably 1.25-1.75. In an embodiment, the upconversion phosphor has a formula of $(Lu_2SiO_5)(LiF)_n:xPr^{3+}$. The n is $(Lu_2SiO_5)(LiF)_n:xPr^{3+}$ is from 0.1-3, preferably 0.25-2.75, preferably 0.5-2.5, preferably 1-2, and preferably 1.25-1.75.

In some embodiments, the upconversion phosphor has a formula selected from the group consisting of $LiYSiO_{3.5}F:xPr^{3+}$, $Li_{1.6}YSiO_{3.5}F_{1.6}:xPr^{3+}$, $Li_{2.5}YSiO_4F_{1.5}:xPr^{3+}$, $Li_2Y_2SiO_5F_2:xPr^{3+}$, $LiY_2Si_{1.5}O_{4.5}F_4:xPr^{3+}$, $Li_{1.5}Y_2SiO_5F_{1.5}:xPr^{3+}$, and $LiLu_2SiO_5F:xPr^{3+}$.

In some embodiments, $LiYSiO_{3.5}F:xPr^{3+}$ is prepared by mixing in the molar proportions $1.0LiF+0.5Y_2O_3+1.0SiO_2$, and when x=0.005, 0.001 mol of $Pr_6O_{11}$ is added. In some embodiments, $Li_{1.6}YSiO_{3.5}F_{1.6}:xPr^{3+}$ is prepared by mixing in the molar proportions $1.6LiF+0.5Y_2O_3+1.0SiO_2$ and when x=0.005, 0.001 mol of $Pr_6O_{11}$ is added. In some embodiments, $Li_2Y_2SiO_5F_2:xPr^{3+}$ is prepared by mixing in the molar proportions $2.0LiF+1.0Y_2O_3+1.0SiO_2$ and when x=0.005, 0.001 mol of $Pr_6O_{11}$ is added. In some embodiments, $LiY_2Si_{1.5}O_{4.5}F_4:xPr^{3+}$ is prepared by mixing in the molar proportions $1.0LiF+0.5Y_2O_3+1.0YF_3+1.5SiO_2$ and when x=0.005, 0.001 mol of $Pr_6O_{11}$ is added. In some embodiments, $LiLu_2SiO_5F:xPr^{3+}$ is prepared by mixing in the molar proportions $1.0LiF+1.0Lu_2O_3+1.0SiO_2$ and when x=0.005, 0.001 mol of $Pr_6O_{11}$ is added.

In some embodiments, the upconversion phosphor has at least one crystal phase selected from the group consisting of $LiY_3(SiO_4)_3F_2$ and $\beta-Y_2Si_2O_7$, when R is Y. In a preferred embodiment, the upconversion phosphor has only a $LiY_3(SiO_4)_3F_2$ crystal phase, when R is Y.

In some embodiments, the upconversion phosphor has a powder particle size of 5-20 micrometers (μm), preferably 6-19 μm, preferably 7-18 μm, preferably 8-17 μm, preferably 9-16 μm, preferably 10-15 μm, preferably 11-14 μm, and preferably 12-13 μm.

A method of upconverting light is described. The method includes irradiating the upconversion phosphor with light. The light is from a broadband light source from 300-625 nanometers (nm), preferably 325-600 nm, preferably 350-575 nm, preferably 375-550 nm, preferably 400-525 nm, preferably 425-500 nm, preferably 430-480 nm, and preferably 450-475 nm. In a preferred embodiment, the light is selected from the group consisting of normal natural sunlight, concentrated natural sunlight, simulated sunlight, or a mix of LED light, thereby preventing the need for expensive light sources. The light has a power density of 0.1-1000 milliwatts per centimeter square ($mW/cm^2$), preferably 1-950 $mW/cm^2$, preferably 100-900 $mW/cm^2$, preferably 200-800 $mW/cm^2$, preferably 300-700 $mW/cm^2$, and preferably 400-600 $mW/cm^2$.

In preferred embodiments, the phosphor is capable of being activated by simulated sunlight from a solar simulator, such as a power-tunable fiber solar simulator whose output can be tuned between 0.1 sun and 20 suns, preferably 1-18 suns, 2-16 suns, 4-14 suns, 6-12 suns, or 8-10 suns. Herein, the term "activated" refers to the phosphor upconverting the provided light to a shorter wavelength. In preferred embodiments, the phosphor is capable of being activated by LEDs, including visible-light (400-625 nm) LEDs, UV (300-400 nm) LEDs, and combinations of LEDs with different wavelengths. In preferred embodiments, the phosphor is capable of being activated by monochromatic visible-light laser diodes; the phosphor is capable of being activated by low-intensity monochromatic visible-light laser diodes, such as a 450 nm blue laser diode with output intensity as low as 5 $mW/cm^2$. In preferred embodiments, the phosphor disclosed herein can be more effectively activated by mixing long-wavelength light (430-480 nm, preferably 440-470 nm, and preferably 450-460 nm or 560-625 nm, preferably 575-610, preferably 590-605 nm) with short-wavelength light (300-430 nm, preferably 320-410, preferably 340-390, and preferably 360-370 nm). For example, the UVC luminescence intensity activated by a combination of 450 nm and 365 nm LEDs can be 1-3 orders of magnitude stronger than that activated by a 450 nm LED alone; the phosphor cannot be activated by a yellow LED regardless of the output power. However, the addition of a 365 nm UV LED or a 405 nm violet LED can produce strong upconversion UVC luminescence.

Phosphor materials disclosed herein can effectively upconvert low-energy visible light into higher-energy UVC radiation. Upon irradiating, the upconversion phosphor converts the light to a shorter wavelength light (higher energy light). In some embodiments, the shorter wavelength light has a wavelength in a range of 250-350 nm, preferably 260-340 nm, preferably 270-330 nm, preferably 280-320 nm, and preferably 290-310 nm. In some embodiments, the shorter wavelength light has a maximum peak wavelength in a range of 255-270 nm, preferably 256-269 nm, preferably 257-268 nm, preferably 258-267 nm, preferably 259-266 nm, preferably 260-265 nm, preferably 261-264 nm, and preferably 262-263 nm.

In some embodiments, the shorter wavelength light produced by the phosphor is capable of disinfecting a surface or a solution. Therefore, the upconversion phosphor may be included in different compositions as will be described below to provide disinfecting properties. The phosphors described in the present disclosure may be used in a variety of applications, such as in UVC luminous paints, in making UVC LEDs, and as a sustainable UVC radiation source for outdoor disinfection, water purification, wastewater treatment, photocatalysis, and hydrogen production.

In some embodiments, the upconversion phosphor is dispersed in water and is still able to provide upconverted light. The water may be tap water, distilled water, bidistilled water, deionized water, deionized distilled water, reverse osmosis water, seawater, wastewater, and swimming pool water, at a depth of up to 3.15 m. In preferred embodiments, a phosphor, as disclosed herein, is chemically stable in tap water, seawater, wastewater, and swimming pool water.

In an embodiment, a paint is described. The paint comprises the upconversion phosphor and a fluoropolymer or silicone. The upconversion phosphor powder can be mixed with UVC-transparent and UVC-resistant fluoropolymers and silicones to form a UC UVC luminescent paint. The mixing may be carried out manually or with the help of a stirrer. Suitable examples of fluoropolymers include CyclA-Flo Clear-CF3 amorphous fluoropolymers (Chromis Technologies, New Jersey, U.S.A.), polyvinylfluoride (PVF), polyvinylidene fluoride (PVDF), polytetrafluoroethylene (PTFE), polychlorotrifluoroethylene (PCTFE), fluorinated ethylene-propylene, and polyethylenetetrafluoroethylene (ETFE). The silicones include, for example, QSil 216 and QSil 214 silicones (GHT Group, Tubingen, Germany). Such luminescent paints can be coated onto any solid surfaces, including building walls, swimming pool walls, boards, benches, rocks, trees, ships, vehicles, etc., endowing these surfaces with the capability of emitting UVC radiation when exposed to sunlight and LEDs. Such paints can also be coated onto a visible-light LED chip and can, therefore, conveniently convert a visible-light LED into a UVC LED.

EXAMPLES

The following examples demonstrate praseodymium ($Pr^{3+}$) doped upconversion (UC) phosphors, which may be excited by sunlight to radiate ultraviolet-C (UVC). The examples are provided solely for illustration and are not to be construed as limitations of the present disclosure, as many variations thereof are possible without departing from the spirit and scope of the present disclosure.

Example 1: Method of Preparation of UVC UC Phosphors Li—R—Si—O—F:xPr$^{3+}$

The Li—R—Si—O—F:xPr$^{3+}$ phosphor is a mixture of a silicate and lithium fluoride (LiF), where R may be yttrium (Y) or lutetium (Lu). Hence, the mixture may be a yttrium silicate or a lutetium silicate such as $LiYSiO_4$, $Y_2SiO_5$, $LiLuSiO_4$, or $Lu_2SiO_5$. Oxides of Y and Lu, such as yttrium oxide ($Y_2O_3$) and lutetium oxide ($Lu_2O_3$), may provide Y and Lu, respectively. Further, in some phosphors, fluorides of Y and Lu, such as yttrium fluoride ($YF_3$) and lutetium(III) fluoride, may also provide Y and Lu, respectively, to tune the concentration of fluorine (F) in the materials. Lithium (Li) is provided by lithium fluoride (LiF) and lithium carbonate ($Li_2CO_3$). Fluorides such as LiF, $YF_3$, or $LuF_3F$ may provide F. Silicon dioxide ($SiO_2$) may provide silicon (Si). All the constituent elements, such as Li, R, Si, O, and F, may be fine-tuned with wide ranges. The concentration of trivalent praseodymium ion ($Pr^{3+}$) is 0.01 to 5, preferably 0.1 to 3, and represents the mole percentage based on the total moles of the phosphor.

In making a specific phosphor, a mixture of components such as the oxides, the fluorides, and the carbonates, in stoichiometric amounts, were ground to form a homogeneous powder for pre-firing. The mixed powder was placed in an alumina crucible and covered with a lid. The covered alumina crucible was then placed inside a bigger alumina crucible filled with a specific amount of graphite powder and covered with a lid. The mixed powder was then pre-fired in a muffle furnace at 600 degrees Celsius (° C.) to 700° C. for 2 hours (h) to 3 h. The graphite powder provided a weak reducing environment to prevent the oxidation of $Pr^{3+}$ to $Pr^{4+}$. The pre-fired material was further ground to a fine powder suitable for sintering. The ground pre-fired powder was pressed into disks of diameters ranging from 15 millimeters (mm) or 40 mm using dies and a hydraulic press. The ground pre-fired powder was also sintered in fluent powder form. Further, the disk or the powder was placed in an alumina crucible and covered with a lid. The covered alumina crucible was placed inside a bigger alumina crucible filled with a specific amount of graphite powder and covered with a lid. The disk or powder was then sintered in a muffle furnace at 800° C. to 1000° C. for 2 h to 3 h to form solid ceramic disks or fluent powder.

Example 2: Characterization of LiYSiO$_{3.5}$F:Pr$^{3+}$ Phosphors

The methods and phosphors disclosed herein are exemplified by preparing the phosphor with a nominal composition of LiYSiO$_{3.5}$F:0.005Pr$^{3+}$. LiYSiO$_{3.5}$F:0.005Pr$^{3+}$ phosphor was prepared using the above-described method of mixing the components in the molar proportions given below.

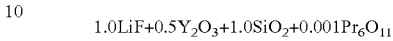

The optical measurements were mainly carried out on the disk samples. Powder samples were used to make luminescent paints.

Figure 1B:
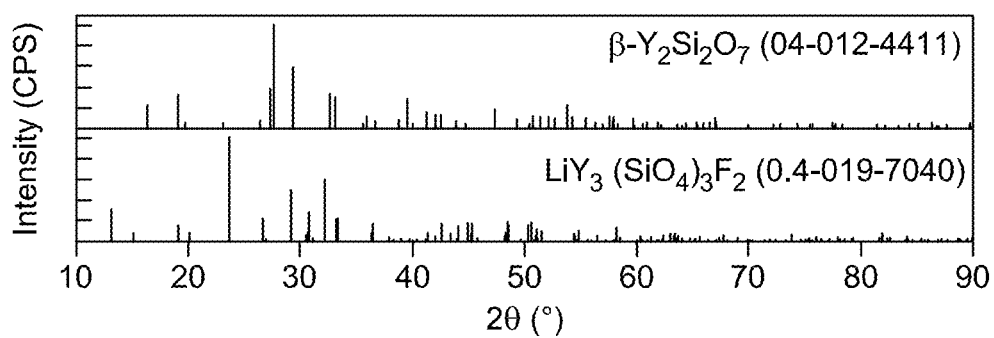
FIG. 1B shows crystalline phases of $LiY_3(SiO_4)_3F_2$ and $\beta-Y_2Si_2O_7$ samples, according to certain embodiments.

FIGS. 1A and 1B show the X-ray diffraction (XRD) pattern of the LiYSiO$_{3.5}$F:0.005Pr$^{3+}$ sample and the crystalline phases, including LiY$_3$(SiO$_4$)$_3$F$_2$ and β-Y$_2$Si$_2$O$_7$.

Figure 2:
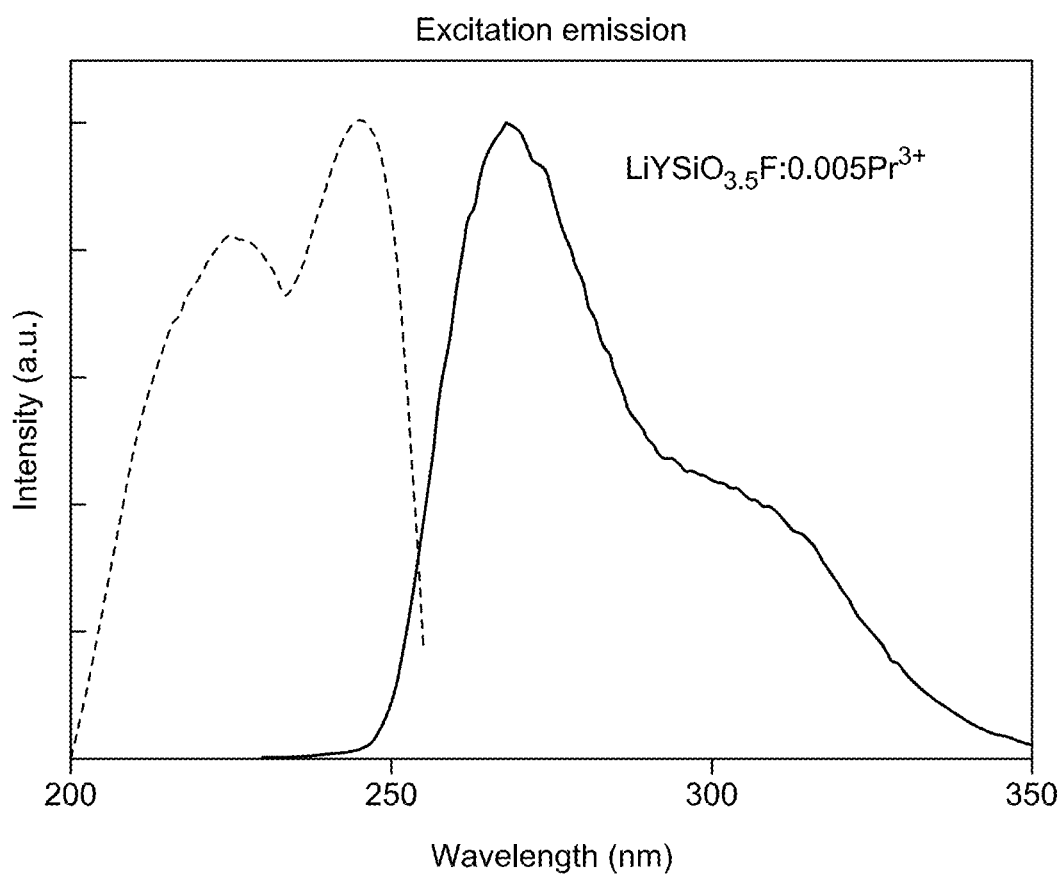
FIG. 2 is a graph showing normalized photoluminescence excitation and emission spectra of a $LiYSiO_{3.5}F:0.005Pr^{3+}$ phosphor, according to certain embodiments.

FIG. 2 shows the normalized photoluminescence excitation and emission spectra of LiYSiO$_{3.5}$F:0.005Pr$^{3+}$ phosphor. The emission spectrum was acquired under 220 nanometers (nm) light excitation, and the excitation spectrum was obtained by monitoring 268 nm emission.

Figure 3:
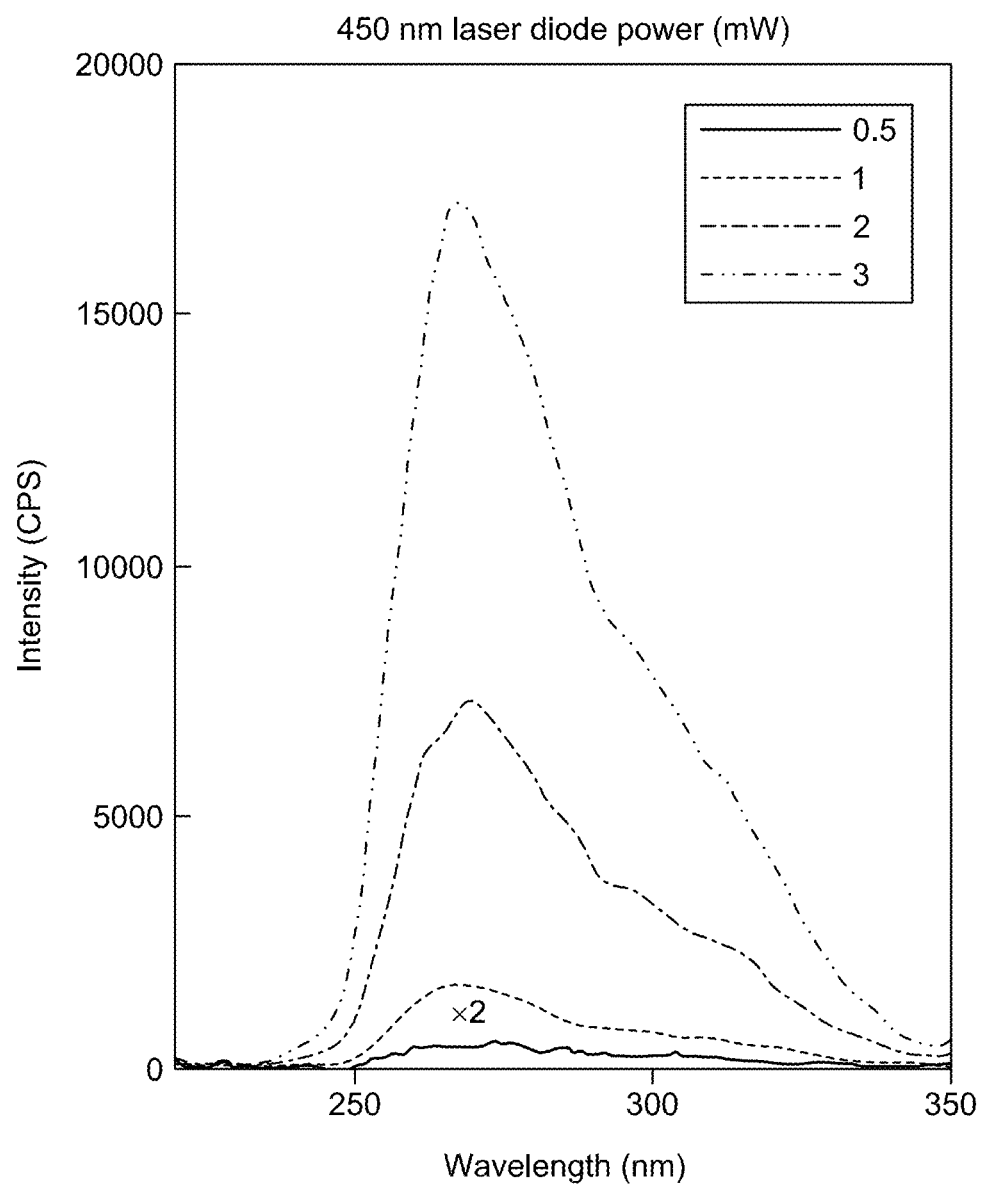
FIG. 3 shows upconversion ultraviolet-C (UVC) emission spectra of $LiYSiO_{3.5}F:0.005Pr^{3+}$ phosphor excited by a 450 nanometers (nm) laser diode at different output powers, according to certain embodiments.

FIG. 3 shows the upconversion UVC emission spectra of LiYSiO$_{3.5}$F:0.005Pr$^{3+}$ phosphor when excited by a 450 nm laser diode at output powers of 0.5 milliwatts (mW), 1 mW, 2 mW, and 3 mW. The laser beam was 0.1 square centimeters (cm$^2$).

Figure 4A:
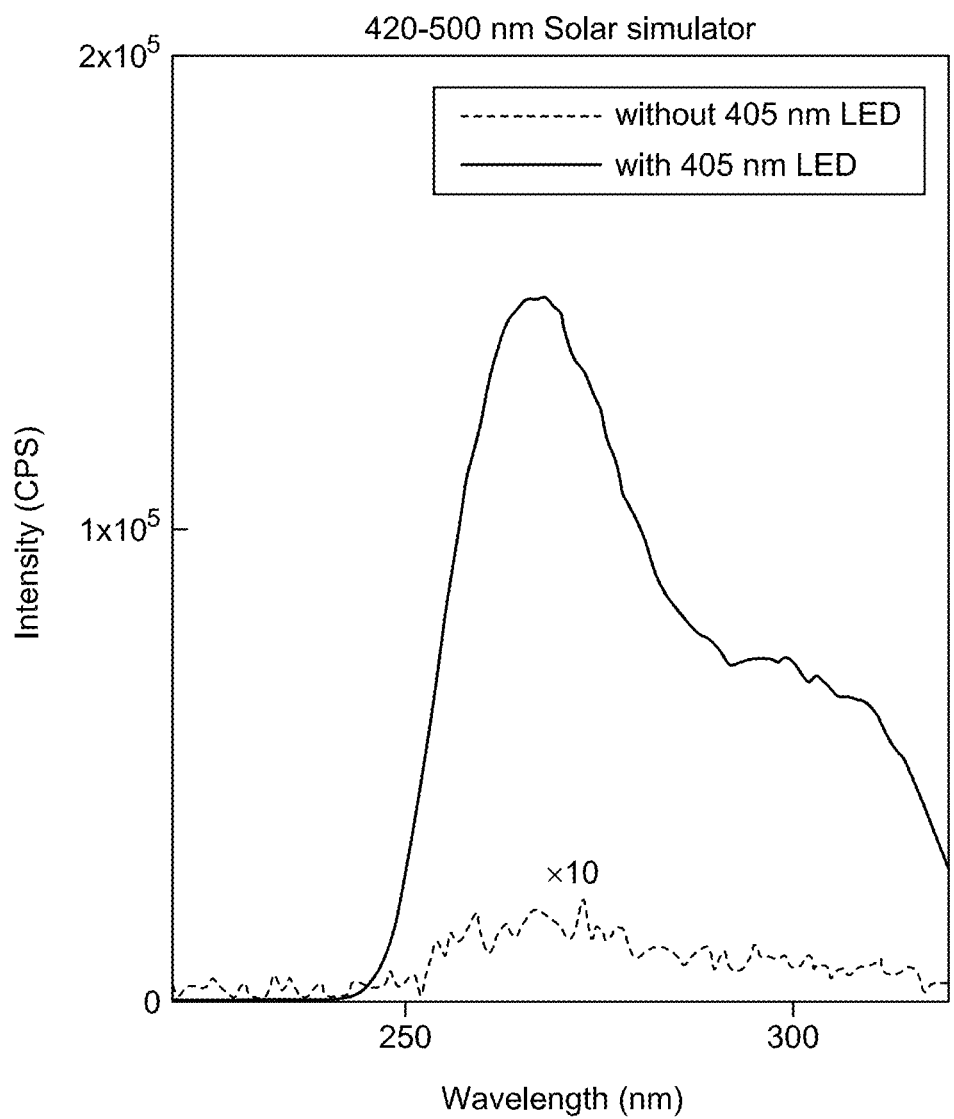
FIG. 4A is a graph showing the upconversion UVC emission spectra of $LiYSiO_{3.5}F:0.005Pr^{3+}$ phosphor excited by a 440 nm to 500 nm band of a solar simulator with and without a 405 nm light emitting diode (LED) light, according to certain embodiments.
Figure 4B:
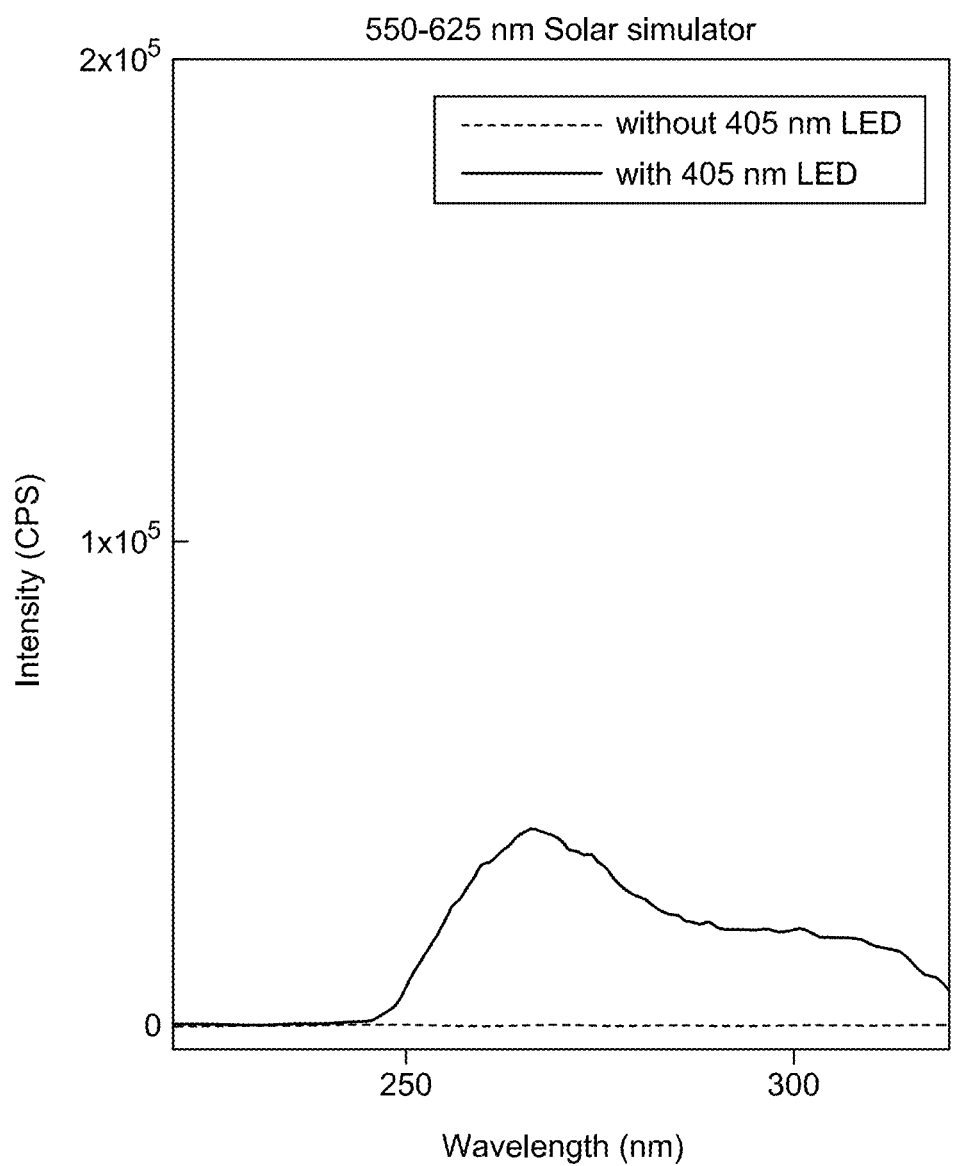
FIG. 4B is a graph showing the upconversion UVC emission spectra of $LiYSiO_{3.5}F:0.005Pr^{3+}$ phosphor excited by a 550 nm to 625 nm band of a solar simulator with and without a 405 nm LED light, according to certain embodiments.

FIG. 4A shows the upconversion UVC emission spectra of the LiYSiO$_{3.5}$F:0.005Pr$^{3+}$ phosphor when excited by a 440 nm to 500 nm band of a solar simulator with and without a 405 nm light emitting diode (LED) light. FIG. 4B shows the upconversion UVC emission spectra of the LiYSiO$_{3.5}$F:0.005Pr$^{3+}$ phosphor when excited by a 550 nm to 625 nm band of a solar simulator with and without a 405 nm LED light. The overall output intensity of the solar simulator in both cases was set at 1 sun. The intensity of the 405 nm LED at 20 mW was about 6.3 milliwatts per square centimeter (mW/cm$^2$).

FIGS. 5A-5L show the upconversion UVC images of a LiYSiO$_{3.5}$F:0.005Pr$^{3+}$ phosphor disk of 15 mm diameter under the excitation of a solar simulator emission band combined with a 365 nm LED. The UVC images were recorded using an Ofil corona camera. FIGS. 5A-5F show the upconversion UVC radiation when a LiYSiO$_{3.5}$F:0.005Pr$^{3+}$ phosphor disk was excited with a 440 nm to 500 nm solar band combined with the 365 nm LED tuned to different intensities. Further, pure 440 nm to 500 nm solar band excitation and pure 365 nm LED excitation are also shown. The optical gain (OG) of the corona camera was set at 100. FIGS. 5G-5L show the upconversion UVC radiation when the LiYSiO$_{3.5}$F:0.005Pr$^{3+}$ phosphor disk was excited with a 550 nm to 625 nm solar band combined with a 365 nm LED tuned to different intensities. Further, pure 550 nm to 625 nm solar band excitation and pure 365 nm LED excitation are also shown. The OG of the corona camera was set at 120. The overall output intensity of the solar simulator was set at 1 sun. The 365 nm LED beam intensity was tuned to 0 mW/cm$^2$, 7 mW/cm$^2$, 36 mW/cm$^2$, 72 mW/cm$^2$, 362 mW/cm$^2$, and 726 mW/cm$^2$. The imaging distance from the disk to the camera was 1 meter (m). It was observed that a pure 440 nm to 500 nm solar band produced a weak UVC upconversion emission, while a pure 550 nm to 625 nm solar band did not produce any UVC upconversion emission in LiYSiO$_{3.5}$F:0.005Pr$^{3+}$.

Figure 6A:
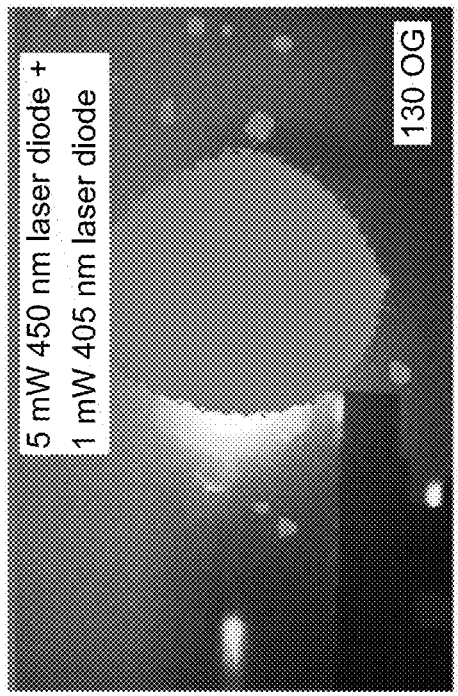
FIG. 6A is an image of upconversion UVC emission of a LiYSiO$_{3.5}$F:0.005Pr$^{3+}$ phosphor disk under the excitation of 5 milliwatts (mW) 450 nm laser diode, according to certain embodiments.
Figure 6B:
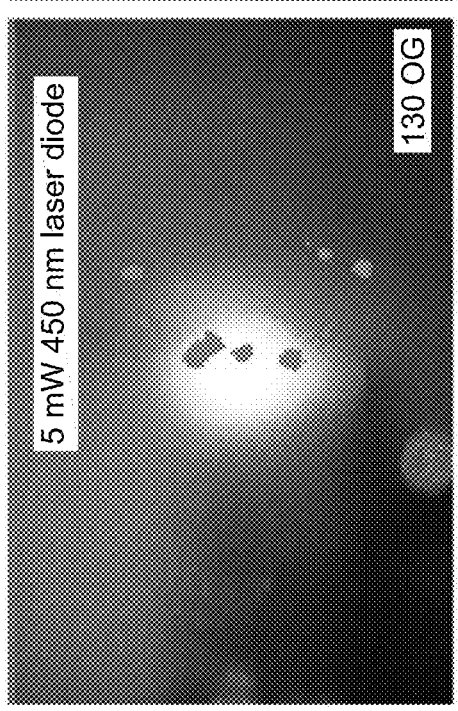
FIG. 6B is an image of upconversion UVC emission of a LiYSiO$_{3.5}$F:0.005Pr$^{3+}$ phosphor disk under combined excitation of 5 mW 450 nm and 1 mW 405 nm laser diodes, according to certain embodiments.
Figure 6C:
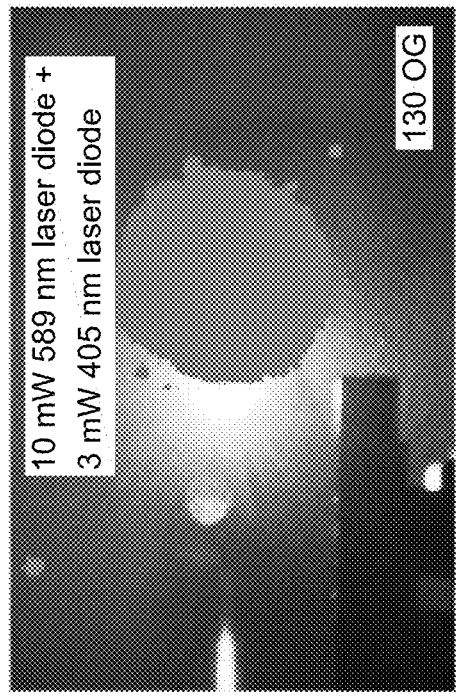
FIG. 6C is an image of upconversion UVC emission of a LiYSiO$_{3.5}$F:0.005Pr$^{3+}$ phosphor disk under the excitation of a 10 mW 589 nm laser diode, according to certain embodiments.
Figure 6D:
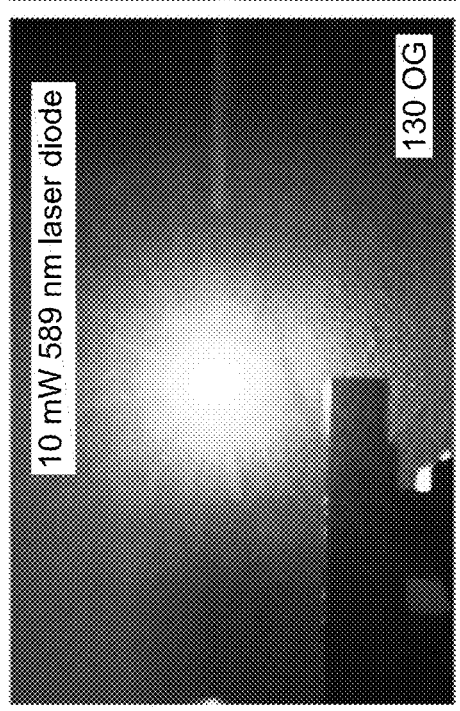
FIG. 6D is an image of upconversion UVC emission of a LiYSiO$_{3.5}$F:0.005Pr$^{3+}$ phosphor disk under combined excitation of 10 mW 589 nm and 3 mW 405 nm laser diodes, according to certain embodiments.

FIGS. 6A-6D show the upconversion UVC images of a LiYSiO$_{3.5}$F:0.005Pr$^{3+}$ disk of 15 mm diameter excited by combined laser diodes of different wavelengths. The UVC images were recorded using an Ofil corona camera. The OG of the corona camera was set at 130, and the imaging distance from the disk to the camera was 1 m. FIG. 6A shows an upconversion UVC radiation when the LiYSiO$_{3.5}$F:0.005Pr$^{3+}$ phosphor disk was excited by a 5 mW 450 nm laser diode. FIG. 6B shows an upconversion UVC radiation when the LiYSiO$_{3.5}$F:0.005Pr$^{3+}$ phosphor disk was excited by a combination of 5 mW 450 nm and 1 mW 405 nm laser diodes. FIG. 6C shows upconversion UVC radiation when the LiYSiO$_{3.5}$F:0.005Pr$^{3+}$ phosphor disk was excited by a 10 mW 589 nm laser diode. FIG. 6D shows upconversion UVC radiation when the LiYSiO$_{3.5}$F:0.005Pr$^{3+}$ phosphor disk was excited by a combination of 10 mW 589 nm and 3 mW 405 nm laser diodes.

Figure 7:
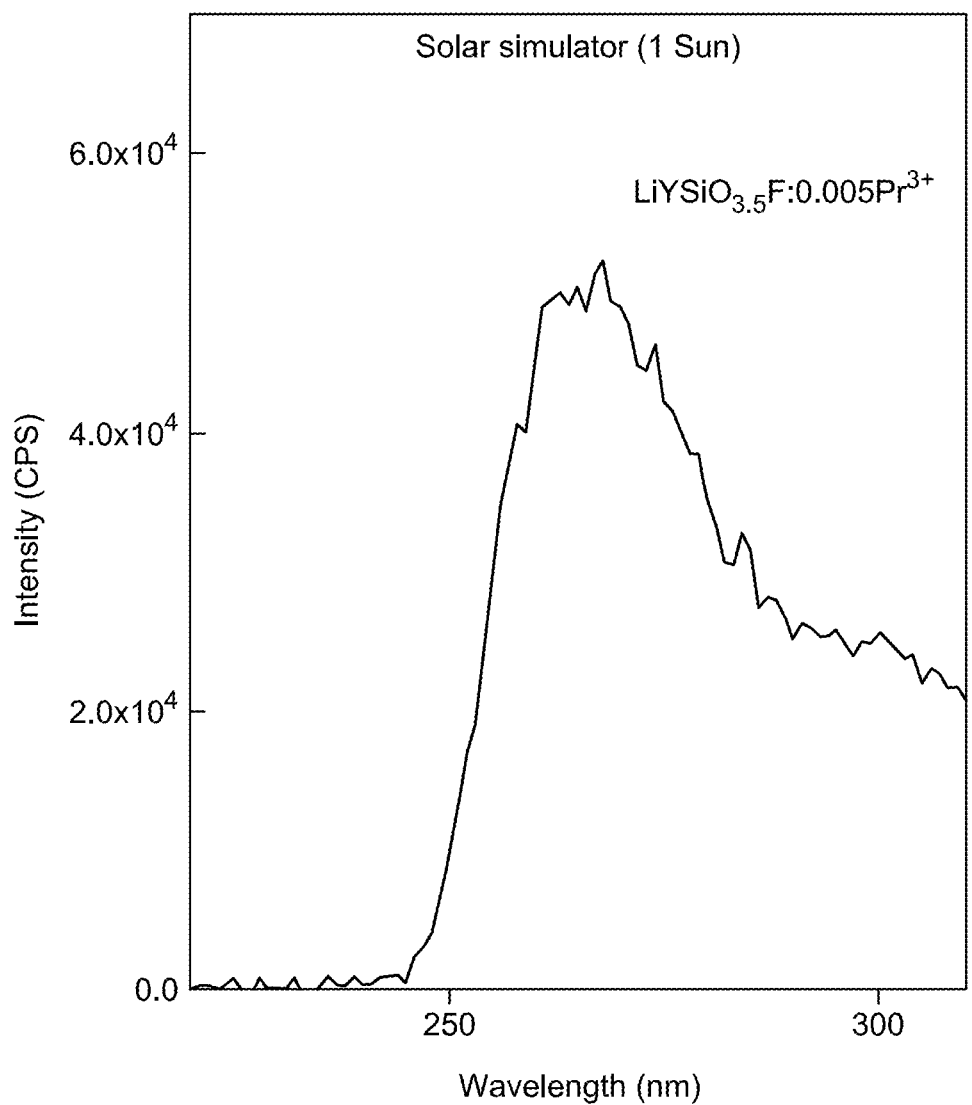
FIG. 7 is a graph showing the upconversion UVC emission spectrum of LiYSiO$_{3.5}$F:0.005Pr$^{3+}$ phosphor when excited by a solar simulator at 1 sun intensity, according to certain embodiments.
Figures 8G, 8H, 8I:
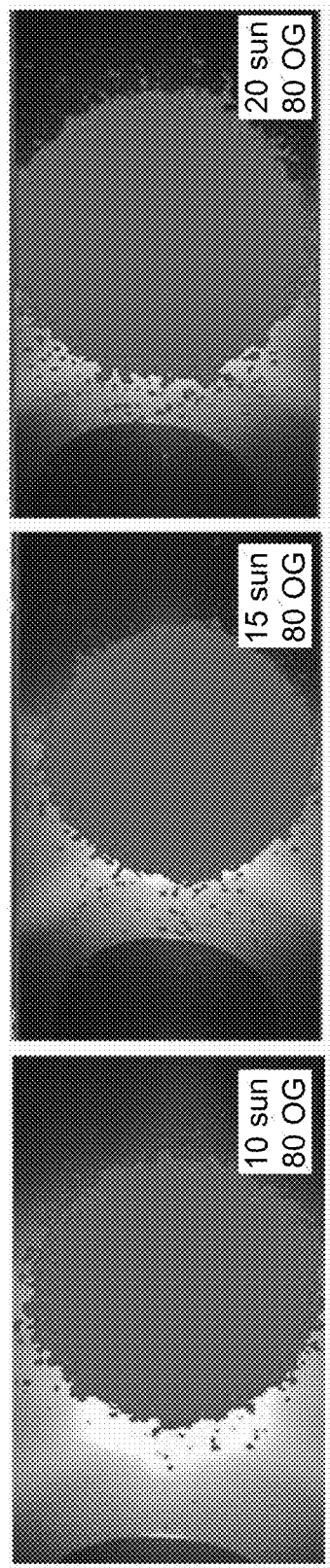
FIG. 8G is an image of upconversion UVC emission of a LiYSiO$_{3.5}$F:0.005Pr$^{3+}$ phosphor disk under irradiation of 10 suns, according to certain embodiments.
FIG. 8H is an image of upconversion UVC emission of a LiYSiO$_{3.5}$F:0.005Pr$^{3+}$ phosphor disk under irradiation of 15 suns, according to certain embodiments.
FIG. 8I is an image of upconversion UVC emission of a LiYSiO$_{3.5}$F:0.005Pr$^{3+}$ phosphor disk under irradiation of 20 suns, according to certain embodiments.

FIG. 7 shows the UVC upconversion emission spectrum of LiYSiO$_{3.5}$F:0.005Pr$^{3+}$ phosphor under the excitation of a solar simulator at 1 sun intensity. A 325 nm long-pass filter was used to block light of wavelength less than 325 nm light from the simulator.

FIGS. 8A-8I show the upconversion UVC images of a 15 mm diameter LiYSiO$_{3.5}$F:0.005Pr$^{3+}$ disk under 0.1-20 sun irradiation using a power-tunable solar simulator system. The position of the disk is indicated by the dashed circle in FIG. 8A. The UVC images were recorded using an Ofil corona camera. The imaging distance from the disk to the camera was 1 m. As the intensity of the irradiation beam was increased, the UVC luminescence brightness increased. The OG of the corona camera was decreased from 130 to 80, to make the UVC luminescence signals visible on the camera screen.

A 40 mm diameter LiYSiO$_{3.5}$F:0.005Pr$^{3+}$ disk as shown in FIGS. 9A-9F and LiYSiO$_{3.5}$F:0.005Pr$^{3+}$ powder as shown in FIGS. 9G-9I was excited by natural sunlight from 7:00 AM to 5:00 PM on a typical Saudi summer day. The UVC images were recorded using an Ofil corona camera. The sample was placed toward the sun. The imaging distance from the disk to the camera was 1 m. The OG of the camera was 120 for the disk sample and 110 for the powder sample.

Figure 10:
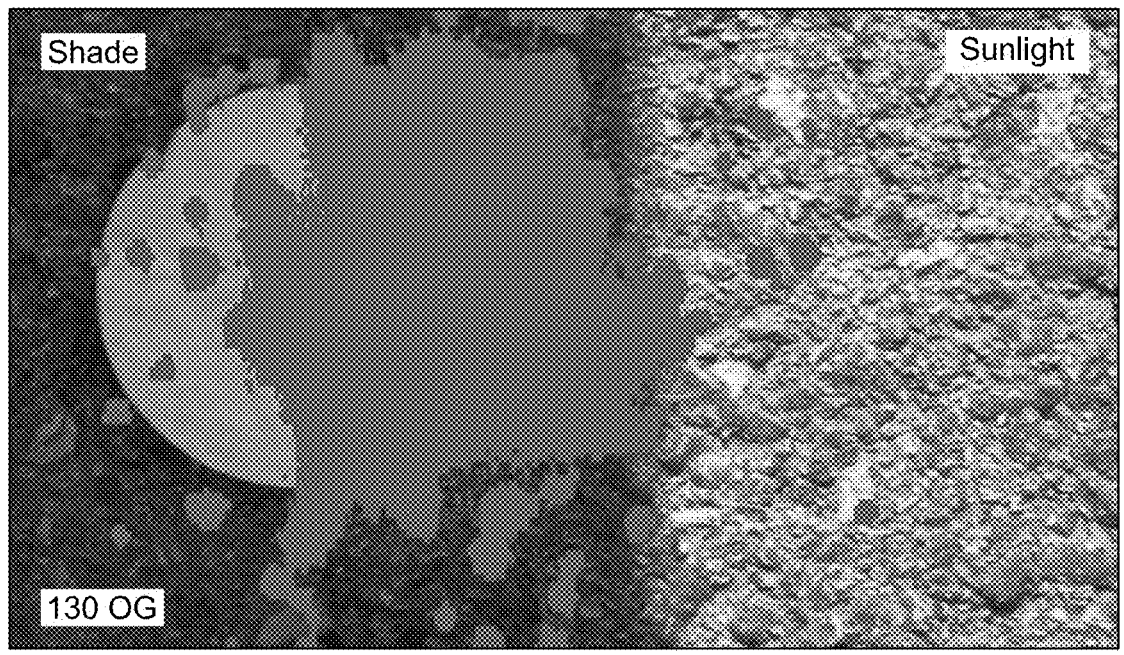
FIG. 10 is an image of upconversion UVC emission of a LiYSiO$_{3.5}$F:0.005Pr$^{3+}$ phosphor disk under excitation of diffused sunlight, according to certain embodiments.

A 40 mm diameter LiYSiO$_{3.5}$F:0.005Pr$^{3+}$ disk was excited by diffused sunlight in the shade, as shown in FIG. 10. The UVC image was recorded using an Ofil corona camera. The imaging distance from the disk to the camera was 1 m. The OG of the camera was 130.

Figure 11A:
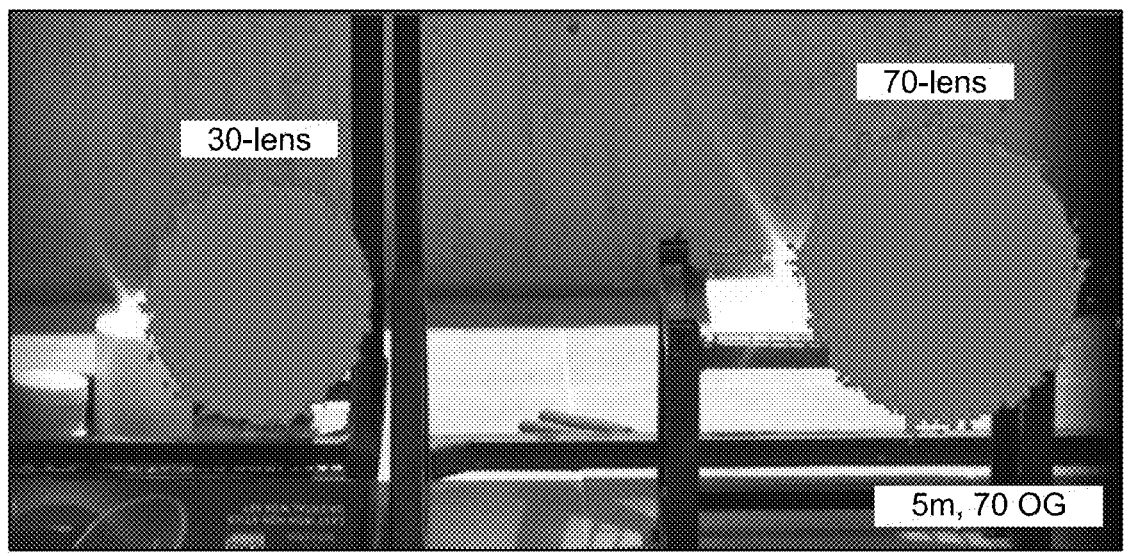
FIG. 11A is an image of upconversion UVC emission of a LiYSiO$_{3.5}$F:0.005Pr$^{3+}$ phosphor disk irradiated by concentrated sunlight with a 30 cm by 30 cm lens (30-lens) and a 70 cm by 70 cm lens (70-lens), according to certain embodiments.
Figure 11B:
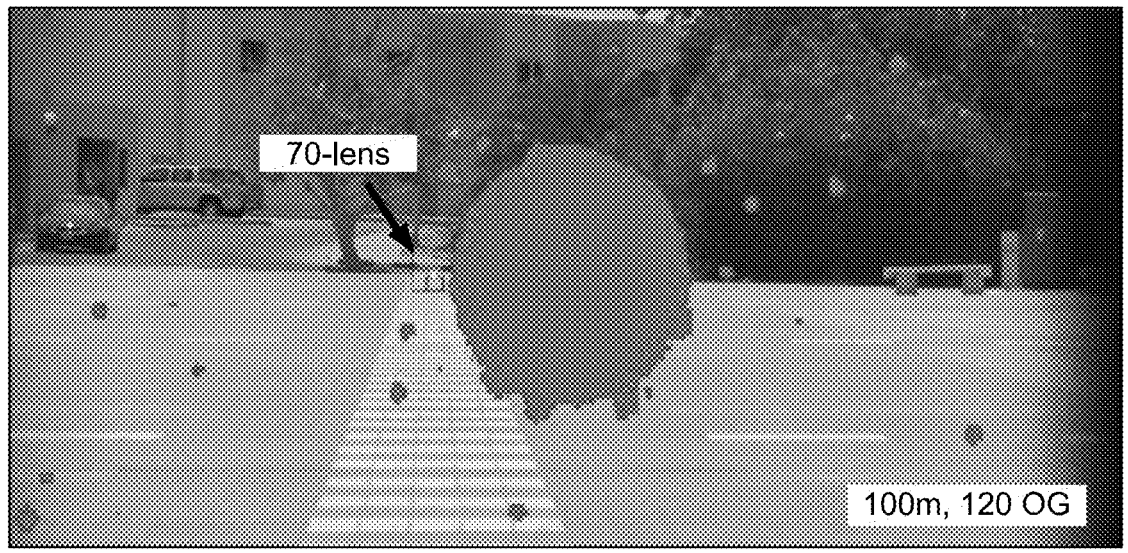
FIG. 11B is an image of upconversion UVC emission of a LiYSiO$_{3.5}$F:0.005Pr$^{3+}$ phosphor disk irradiated by concentrated sunlight with the 70-lens when viewed from a distance of 100 meters (m), according to certain embodiments.
Figure 11C:
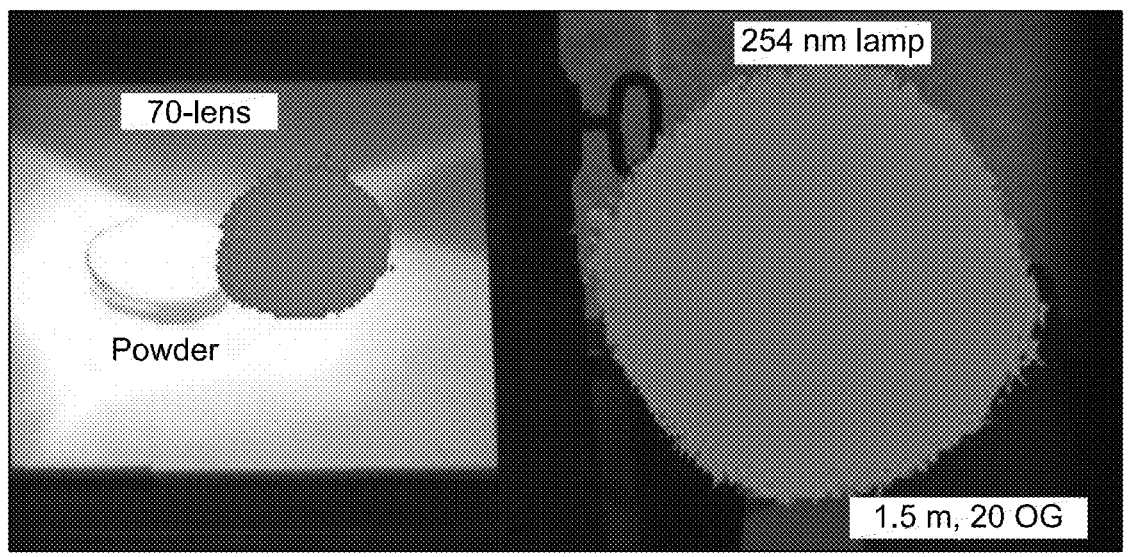
FIG. 11C is an image of upconversion UVC emission of a LiYSiO$_{3.5}$F:0.005Pr$^{3+}$ phosphor disk irradiated by concentrated sunlight with the 70-lens compared to a 4W 254 nm UVC lamp, according to certain embodiments.
Figure 12A:
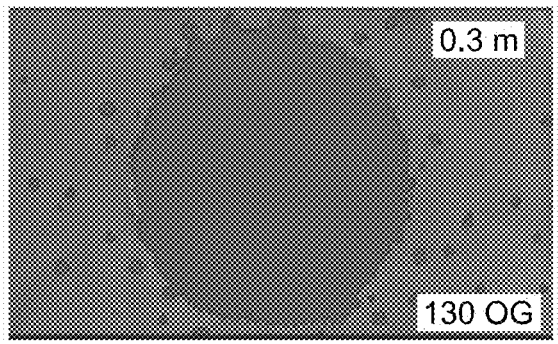
FIG. 12A is an image of upconversion UVC emission of a LiYSiO$_{3.5}$F:0.005Pr$^{3+}$ phosphor disk under the excitation of natural sunlight at a depth of 0.3 m in water, according to certain embodiments.
Figure 12B:
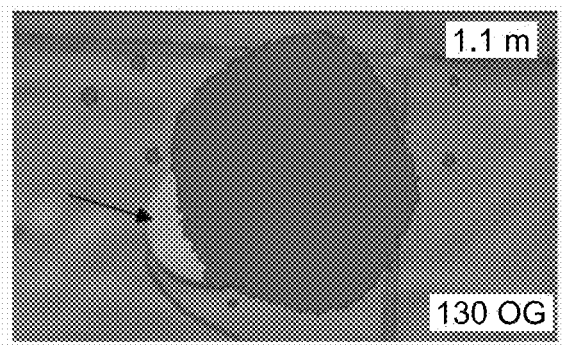
FIG. 12B is an image of upconversion UVC emission of a LiYSiO$_{3.5}$F:0.005Pr$^{3+}$ phosphor disk under the excitation of natural sunlight at a depth of 1.1 m in water, according to certain embodiments.
Figure 12C:
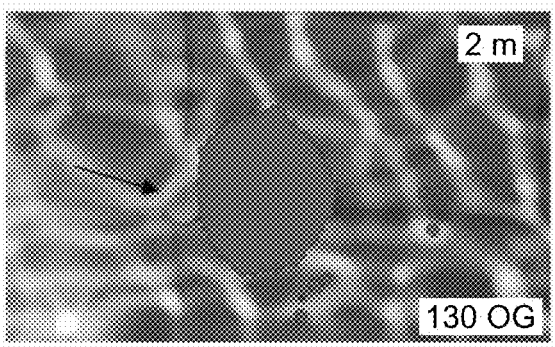
FIG. 12C is an image of upconversion UVC emission of a LiYSiO$_{3.5}$F:0.005Pr$^{3+}$ phosphor disk under the excitation of natural sunlight at a depth of 2 m in water, according to certain embodiments.
Figure 12D:
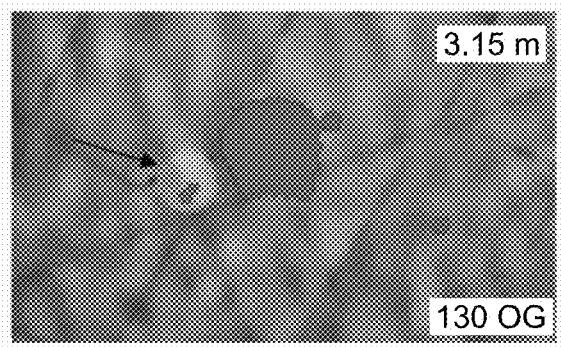
FIG. 12D is an image of upconversion UVC emission of a LiYSiO$_{3.5}$F:0.005Pr$^{3+}$ phosphor disk under the excitation of natural sunlight at a depth of 3.15 m in water, according to certain embodiments.
Figure 12E:
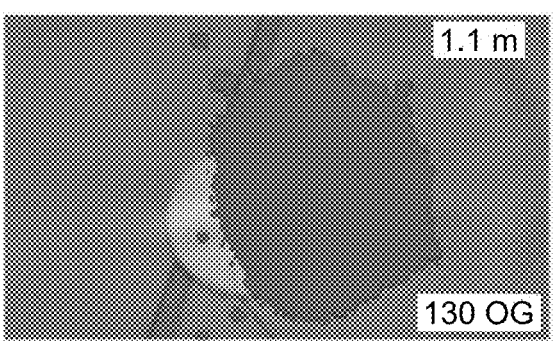
FIG. 12E is an image of upconversion UVC emission of LiYSiO$_{3.5}$F:0.005Pr$^{3+}$ powder thin silicone film, under the excitation of natural sunlight at a depth of 1.1 m in water, according to certain embodiments.
Figure 12F:
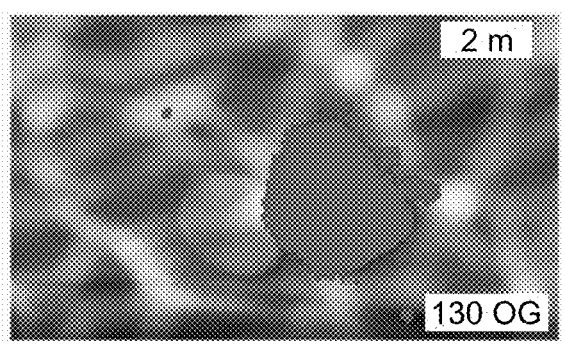
FIG. 12F is an image of upconversion UVC emission of LiYSiO$_{3.5}$F:0.005Pr$^{3+}$ powder thin silicone film, under the excitation of natural sunlight at a depth of 2 m in water, according to certain embodiments.

FIGS. 11A-11C shows the upconversion UVC images of LiYSiO$_{3.5}$F:0.005Pr$^{3+}$ disks and powder irradiated by concentrated sunlight. The UVC image was recorded using an Ofil corona camera. Two Fresnel lenses, a 30 cm by 30 cm lens (30-lens) and a 70 cm by 70 cm lens (70-lens), were used to concentrate the sunlight. The sunlight spots, focused on the samples, were round with a diameter of about 5 mm for the 30-lens and about 10 mm for the 70-lens. The intensities of the concentrated sunlight on the samples were about 3,500 suns for the 30-lens and about 5,500 suns for the 70-lens. FIG. 11A shows both the 30-lens and 70-lens were used to concentrate sunlight on the disk samples. The imaging distance was 5 m, and the OG was 70. FIG. 11B shows the UVC luminescence of a disk excited by 70-lens concentrated sunlight viewed from a distance of 100 m with OG set at 120. FIG. 11C shows the powder sample irradiated by concentrated sunlight using the 70-lens. A 4-W 254 nm mercury UVC lamp was placed aside for comparison. The lamp surface was covered by a blackboard with a 10-mm-diameter hole in the center, which was the same as the focusing spot size of the 70-lens. The imaging distance was 1.5 m, and the OG was 20.

Underwater imaging experiments were conducted at around 1:00 PM on a typical Saudi summer day. FIGS. 12A-12F shows the upconversion UVC images of a 40 mm diameter LiYSiO$_{3.5}$F:0.005Pr$^{3+}$ disk and a 40 mm diameter LiYSiO$_{3.5}$F:0.005Pr$^{3+}$ powder/silicone thin film excited by natural sunlight in water. The UVC images were recorded using an Ofil corona camera. The phosphor disk was immersed in water at a depth of 0.3 m, 1.1 m, 2 m, and 3.15 m. The positions of the disk in water are indicated by arrows in FIGS. 12A-12D. The phosphor powder/silicone thin film was immersed in water at a depth of 1.1 m and 2 m. The thin film was made by mixing 2 grams (g) phosphor powder in 1 g Qsil 216 silicone. The films were about 1 mm thick and about 40 mm in diameter. For all imaging experiments, the distance from the camera to the water surface was 1 m, and the OG for all images was 130.

Figure 13A:
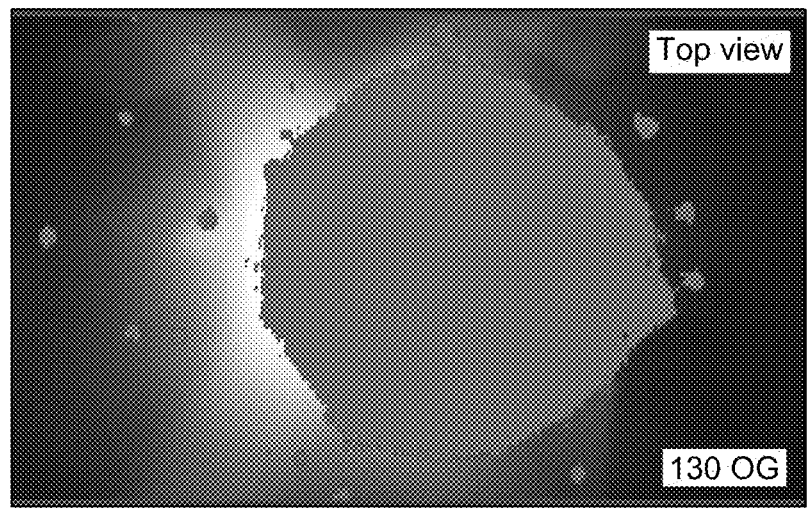
FIG. 13A is the top view of upconversion UVC emission of LiYSiO$_{3.5}$F:0.005Pr$^{3+}$ powder thin silicone film, under the excitation of a white LED flashlight, according to certain embodiments.
Figure 13B:
FIG. 13B is the side view of upconversion UVC emission of LiYSiO$_{3.5}$F:0.005Pr$^{3+}$ powder thin silicone film, under the excitation of a white LED flashlight, according to certain embodiments.

FIG. 13A and FIG. 13B show the upconversion UVC images of a LiYSiO$_{3.5}$F:0.005Pr$^{3+}$ powder/silicone thin film excited by a white LED flashlight. The thin film was made by mixing 1 g phosphor powder in 1 g Qsil 216 silicone. The films were about 1 mm thick and about 40 mm in diameter. The film was placed on the protective glass of an 800-lumen white LED flashlight. The images were recorded using an Ofil corona camera. The imaging distance from the flashlight to the camera was 1 m, and the OG was 130. The results showed that the UVC upconversion phosphor may convert a white LED to a UVC LED.

Example 3: Preparation and Characterization of Li$_{1.6}$YSiO$_{3.5}$F$_{1.6}$:Pr$^{3+}$ Phosphors A Li$_{1.6}$YSiO$_{3.5}$F$_{1.6}$:0.005Pr$^{3+}$ phosphor was prepared using the above-described method of mixing the components in the molar proportions given below.

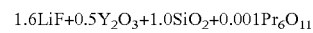

Figure 14A:
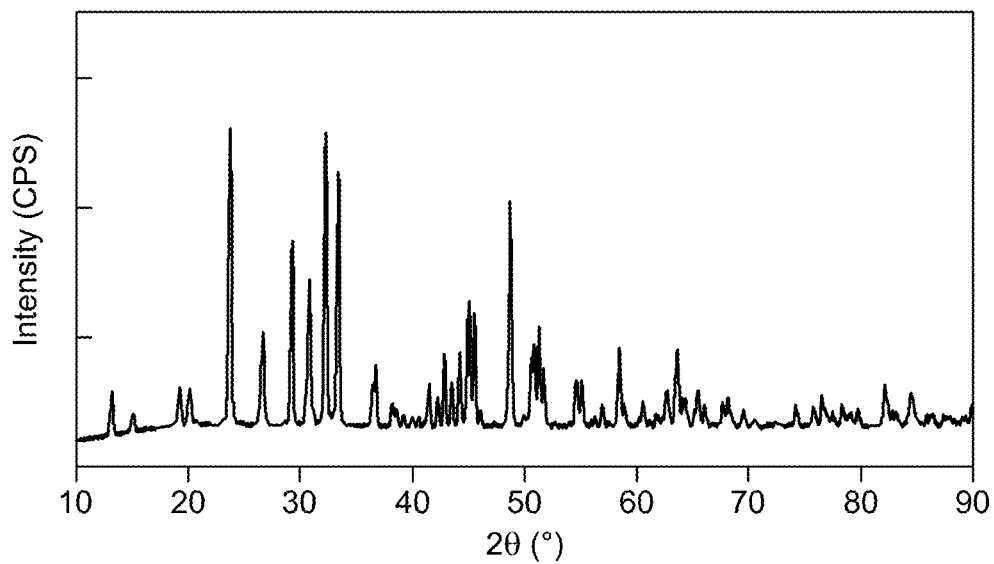
FIG. 14A is a graph showing the XRD pattern of Li$_{1.6}$YSiO$_{3.5}$F$_{1.6}$:0.005Pr$^{3+}$ phosphors, according to certain embodiments.
Figure 14B:
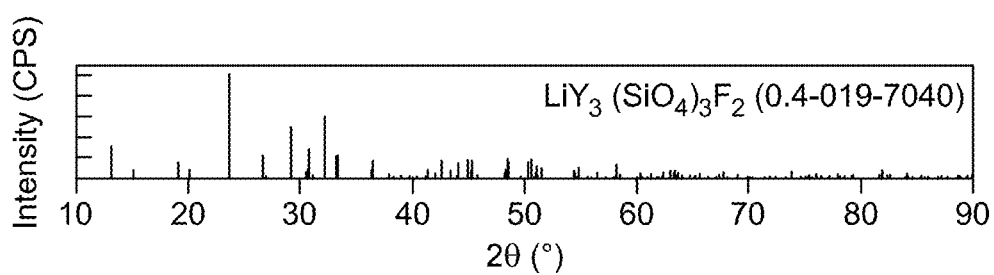
FIG. 14B is a graph showing LiY$_3$(SiO$_4$)$_3$F$_2$ as the main crystalline phase, according to certain embodiments.

FIG. 14A shows the XRD pattern of the Li$_{1.6}$YSiO$_{3.5}$F$_{1.6}$:0.005Pr$^{3+}$ sample. FIG. 14B shows the main crystalline phase as LiY$_3$(SiO$_4$)$_3$F$_2$.

Figure 15A:
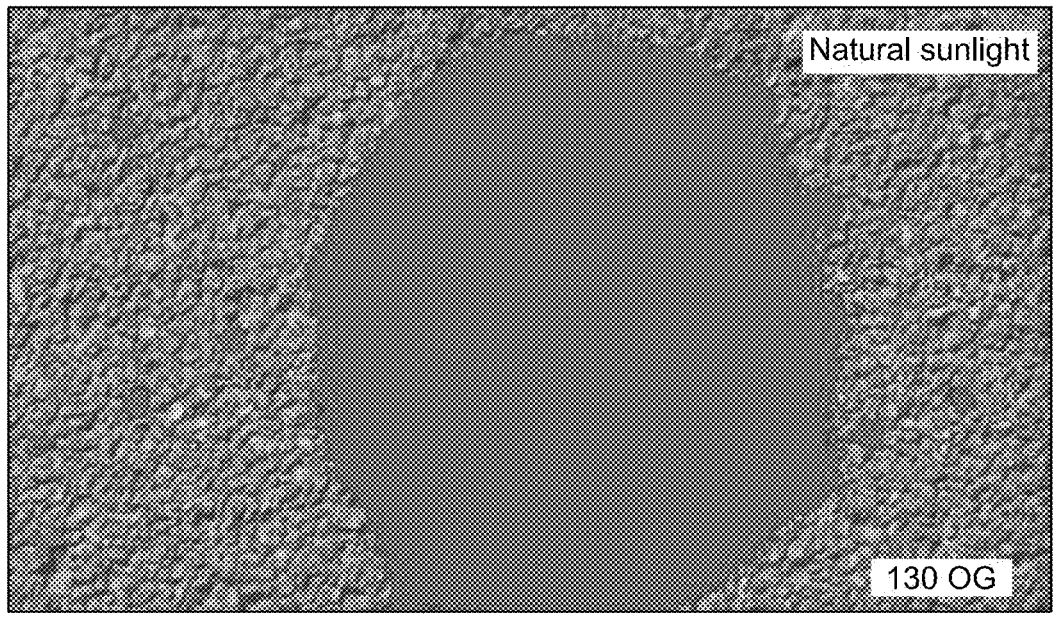
FIG. 15A is an image of upconversion UVC emission of a Li$_{1.6}$YSiO$_{3.5}$F$_{1.6}$:0.005Pr$^{3+}$ phosphor disk under the excitation of normal natural sunlight, according to certain embodiments.
Figure 15B:
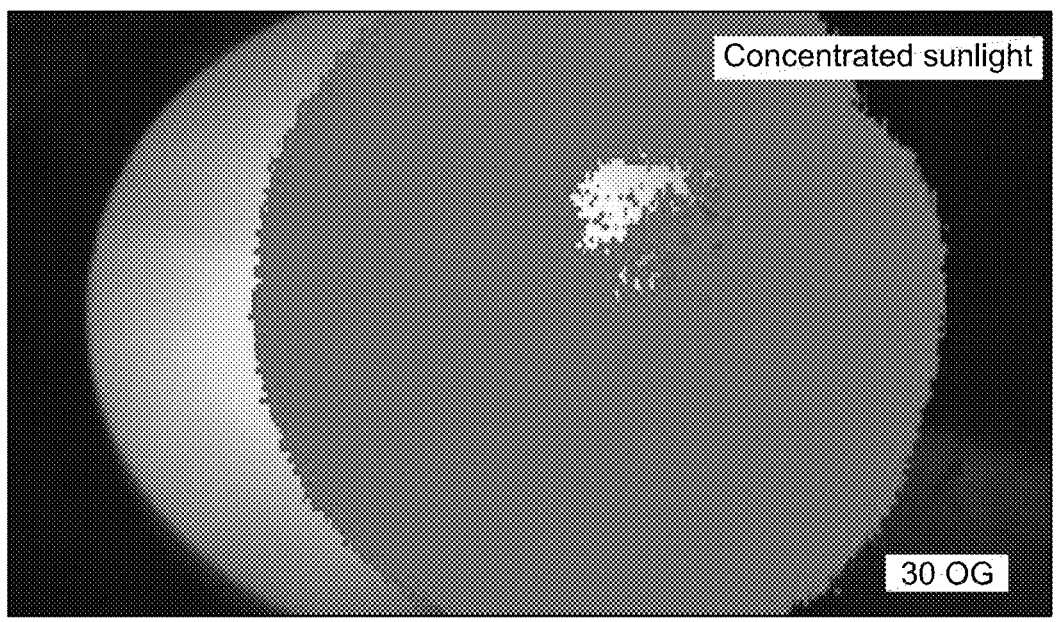
FIG. 15B is an image of upconversion UVC emission of a Li$_{1.6}$YSiO$_{3.5}$F$_{1.6}$:0.005Pr$^{3+}$ phosphor disk under the excitation of concentrated sunlight, according to certain embodiments.
Figure 15C:
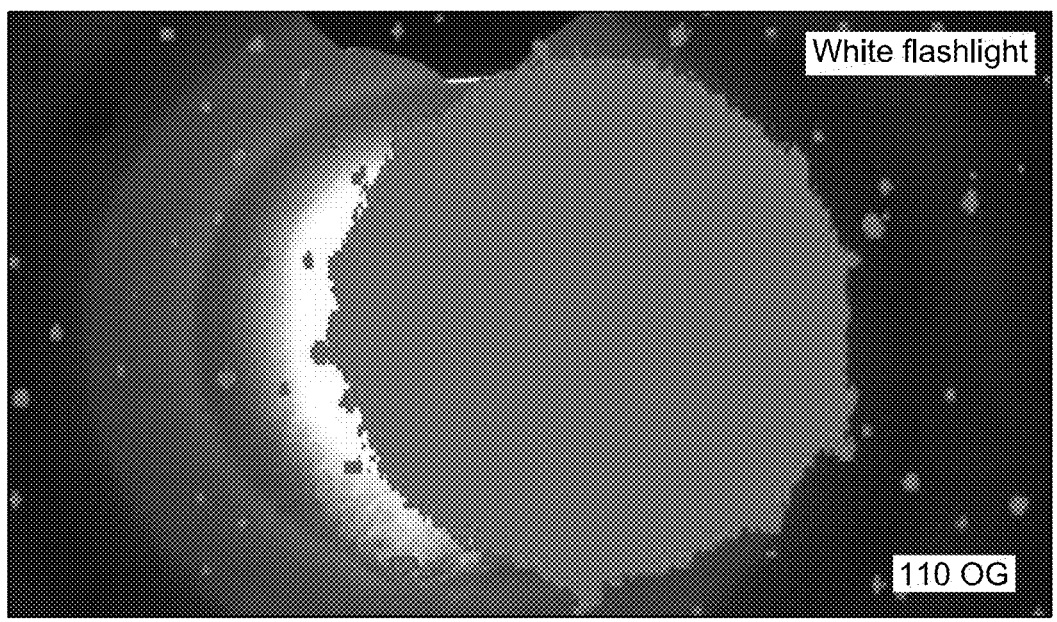
FIG. 15C is an image of upconversion UVC emission of a Li$_{1.6}$YSiO$_{3.5}$F$_{1.6}$:0.005Pr$^{3+}$ phosphor disk under the excitation of a white LED flashlight, according to certain embodiments.

FIGS. 15A-15C show the upconversion UVC images of a 15 mm diameter Li$_{1.6}$YSiO$_{3.5}$F$_{1.6}$:0.005Pr$^{3+}$ disk under the excitation of normal, natural sunlight, concentrated sunlight, and an 800-lumen white LED flashlight. The UVC image was recorded using an Ofil corona camera. The sunlight excitation was conducted at 1:00 PM. The concentrated sunlight was obtained using a 30-lens. The imaging distance from the sample to the camera was 1 m.

Example 4: Preparation and Characterization of Li$_2$Y$_2$SiO$_5$F$_2$:Pr$^{3+}$ Phosphors A phosphor with a nominal composition of Li$_2$Y$_2$SiO$_5$F$_2$:0.005Pr$^{3+}$ was prepared using the above-mentioned method of mixing the components in the molar proportions given below.

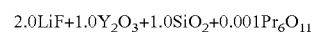

Figure 16A:
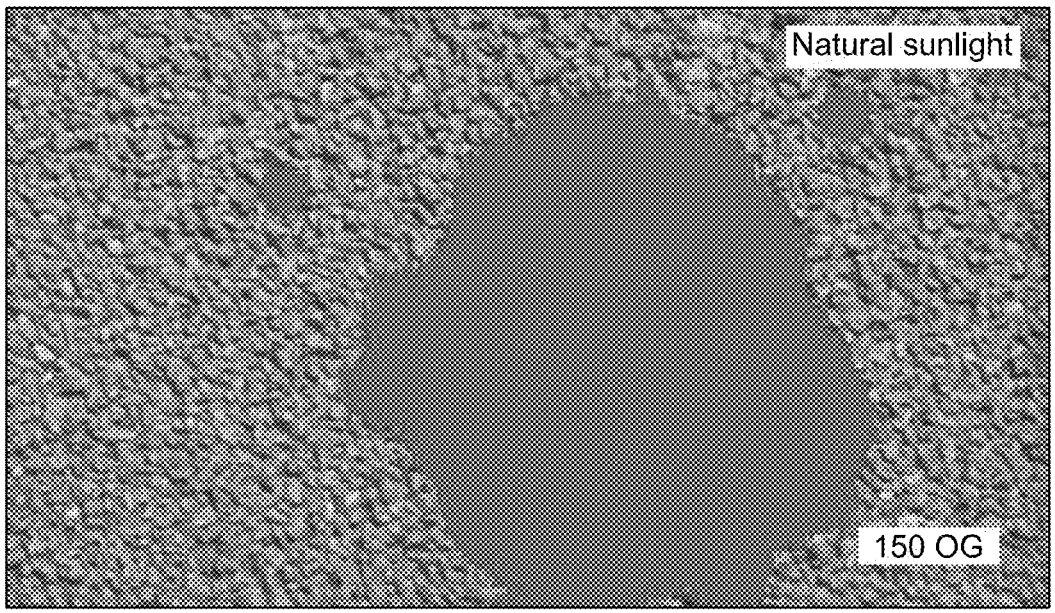
FIG. 16A is an image of upconversion UVC emission of a Li$_2$Y$_2$SiO$_5$F$_2$:0.005Pr$^{3+}$ phosphor disk under the excitation of normal natural sunlight, according to certain embodiments.
Figure 16B:
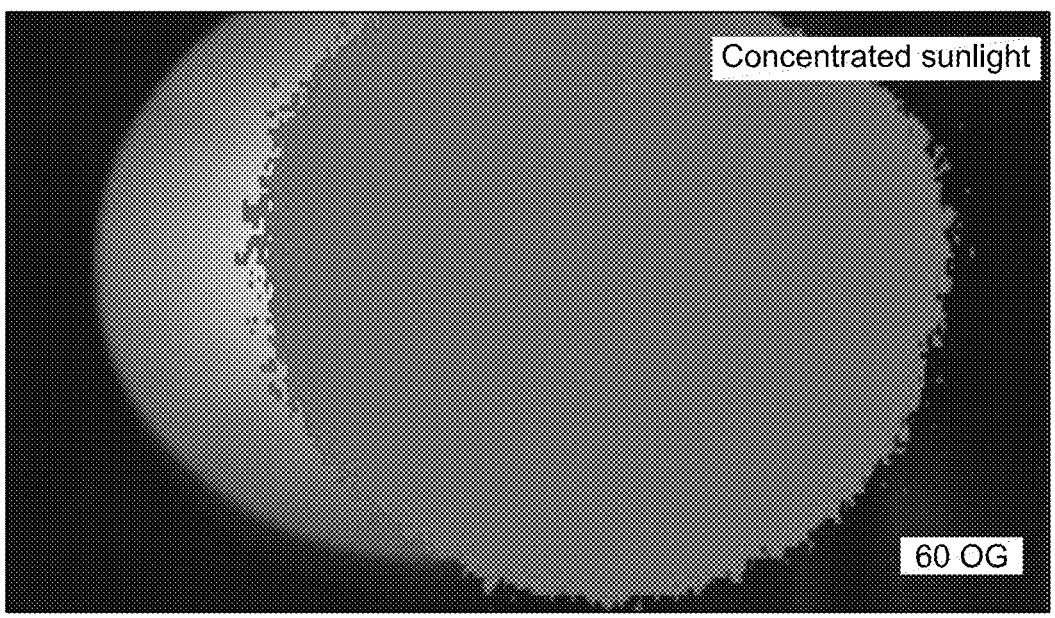
FIG. 16B is an image of upconversion UVC emission of a Li$_2$Y$_2$SiO$_5$F$_2$:0.005Pr$^{3+}$ phosphor disk under the excitation of concentrated sunlight, according to certain embodiments.
Figure 16C:
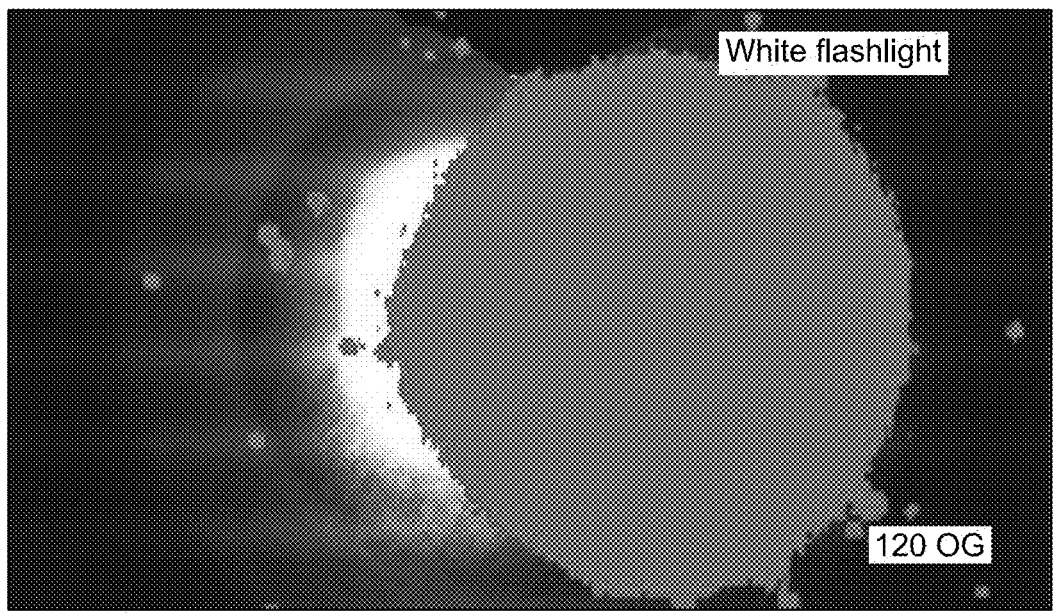
FIG. 16C is an image of upconversion UVC emission of a Li$_2$Y$_2$SiO$_5$F$_2$:0.005Pr$^{3+}$ phosphor disk under the excitation of a white LED flashlight, according to certain embodiments.

FIGS. 16A-16C show the upconversion UVC images of a 15 mm diameter Li$_2$Y$_2$SiO$_5$F$_2$:0.005Pr$^{3+}$ disk excited with normal natural sunlight, concentrated sunlight, and an 800-lumen white LED flashlight. The UVC image was recorded using an Ofil corona camera. The sunlight excitation was conducted at 1:00 PM. The concentrated sunlight was obtained using a 30-lens. The imaging distance from the sample to the camera was 1 m.

Example 5: Preparation and Characterization of LiY$_2$Si$_{1.5}$O$_{4.5}$F$_4$:Pr$^{3+}$ Phosphors A phosphor with a nominal composition of LiY$_2$Si$_{1.5}$O$_{4.5}$F$_4$:0.005Pr$^{3+}$ was prepared using the above-mentioned method of mixing the components in the molar proportions given below.

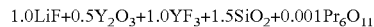

Figure 17A:
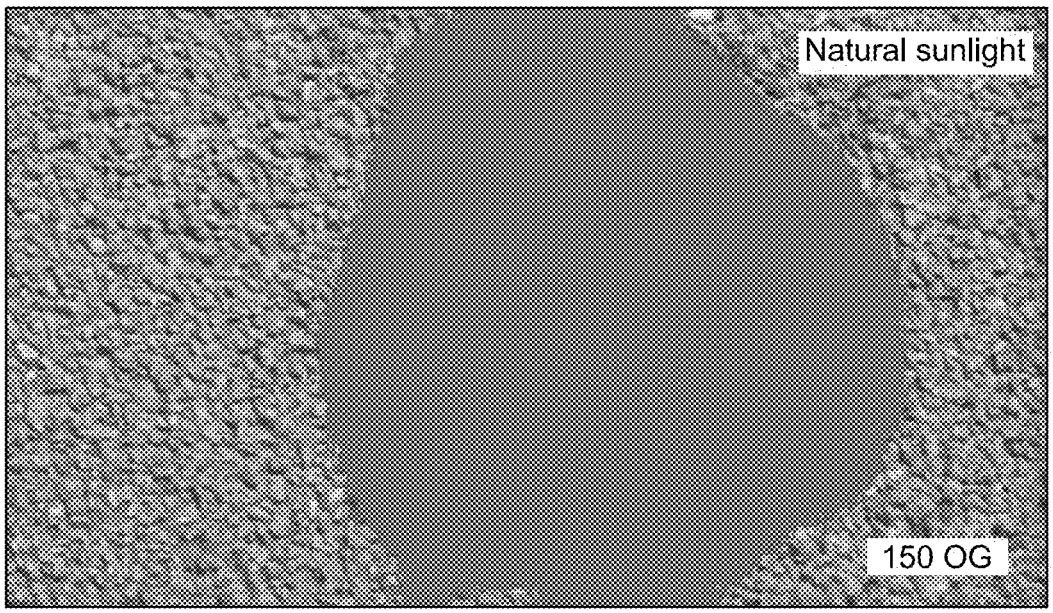
FIG. 17A is an image of upconversion UVC emission of a LiY$_2$Si$_{1.5}$O$_{4.5}$F$_4$:0.005Pr$^{3+}$ phosphor disk under the excitation of normal natural sunlight, according to certain embodiments.
Figure 17B:
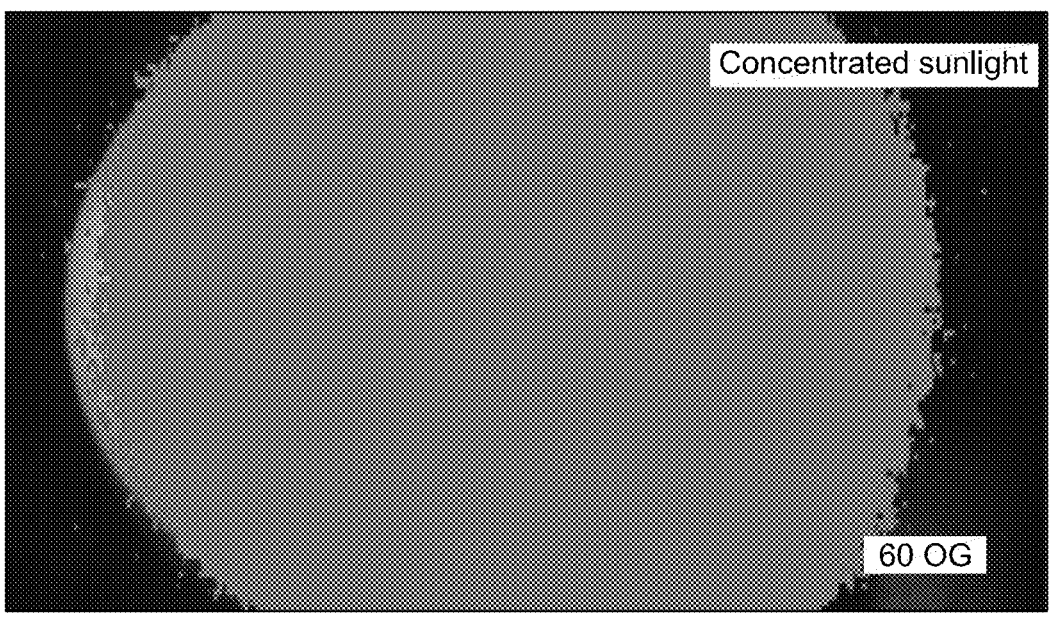
FIG. 17B is an image of upconversion UVC emission of a LiY$_2$Si$_{1.5}$O$_{4.5}$F$_4$:0.005Pr$^{3+}$ phosphor disk under the excitation of concentrated sunlight, according to certain embodiments.
Figure 17C:
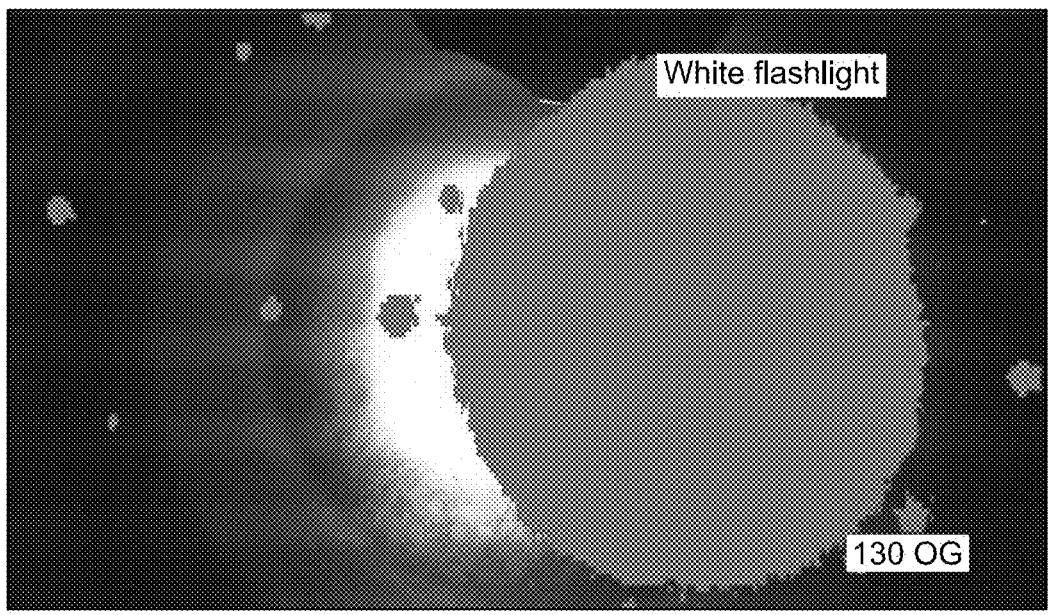
FIG. 17C is an image of upconversion UVC emission of a LiY$_2$Si$_{1.5}$O$_{4.5}$F$_4$:0.005Pr$^{3+}$ phosphor disk under the excitation of a white LED flashlight, according to certain embodiments.

FIGS. 17A-17C show the upconversion UVC images of a 15 mm diameter LiY$_2$Si$_{1.5}$O$_{4.5}$F$_4$:0.005Pr$^{3+}$ disk excited by normal natural sunlight, concentrated sunlight, and an 800-lumen white LED flashlight. The UVC image was recorded using an Ofil corona camera. The sunlight excitation was conducted at 1:00 PM. The concentrated sunlight was obtained using a 30-lens. The imaging distance from the sample to the camera was 1 m.

Example 6: Preparation and Characterization of LiLu$_2$SiO$_5$F:Pr$^{3+}$ Phosphors A phosphor with a nominal composition of LiLu$_2$SiO$_5$F:0.005Pr$^{3+}$ was prepared by the above-mentioned method by mixing the components in the molar proportions given below.

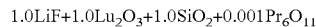

Figure 18A:
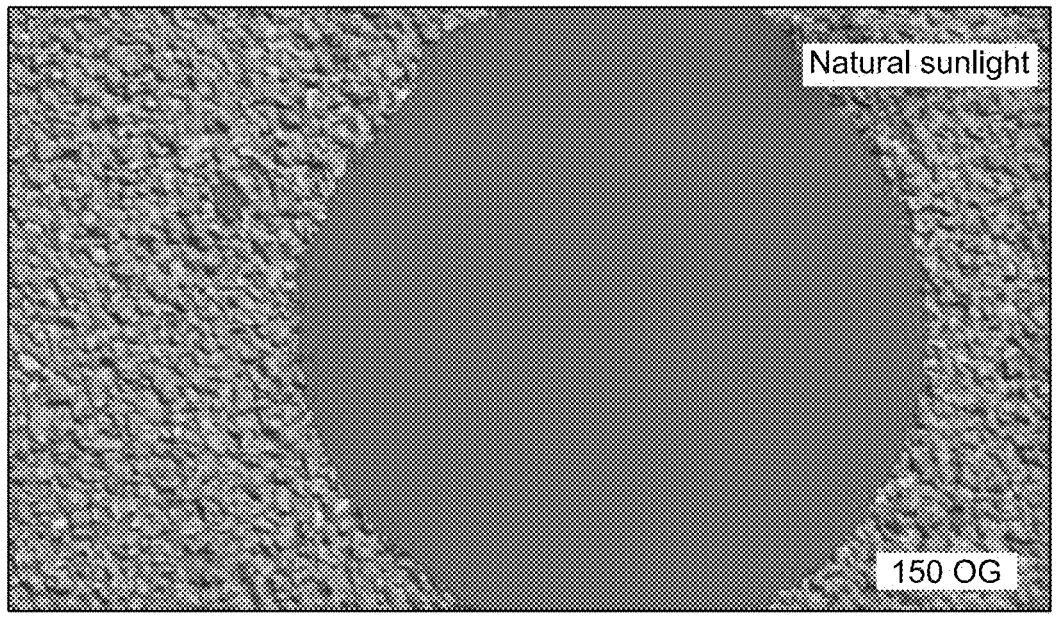
FIG. 18A is an image of upconversion UVC emission of a LiLu$_2$SiO$_5$F:0.005Pr$^{3+}$ phosphor disk under the excitation of normal natural sunlight, according to certain embodiments.
Figure 18B:
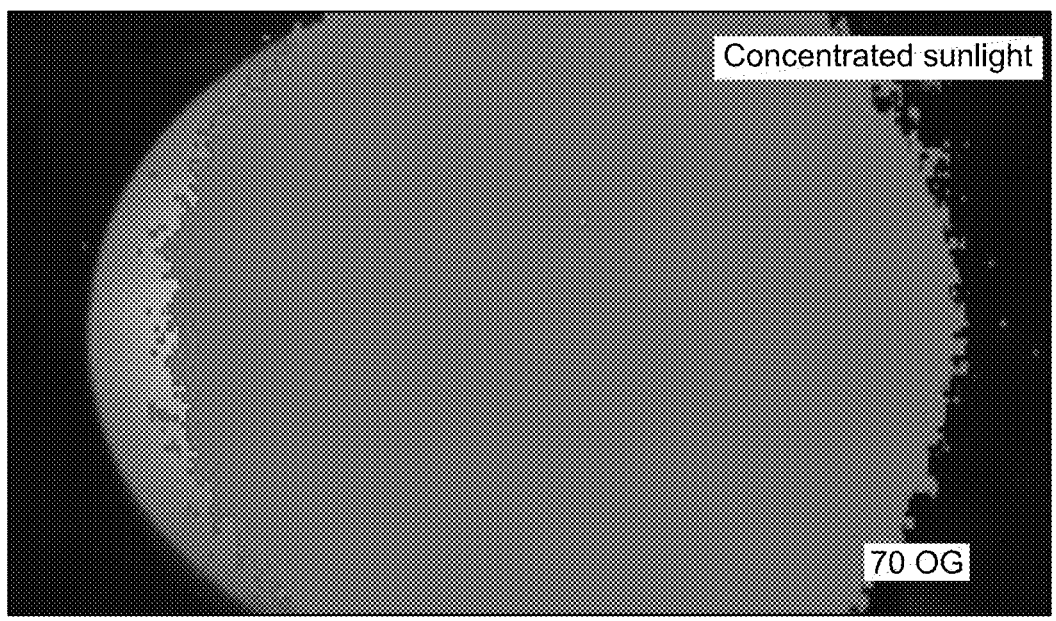
FIG. 18B is an image of upconversion UVC emission of a LiLu$_2$SiO$_5$F:0.005Pr$^{3+}$ phosphor disk under the excitation of concentrated sunlight, according to certain embodiments.
Figure 18C:
FIG. 18C is an image of upconversion UVC emission of a LiLu$_2$SiO$_5$F:0.005Pr$^{3+}$ phosphor disk under the excitation of a white LED flashlight, according to certain embodiments.

FIGS. 18A-18C show the upconversion UVC images of a 15 mm diameter LiLu$_2$SiO$_5$F:0.005Pr$^{3+}$ disk excited by normal natural sunlight, concentrated sunlight, and an 800-lumen white LED flashlight. The UVC image was recorded using an Ofil corona camera. The sunlight excitation was conducted at 1:00 PM. The concentrated sunlight was obtained using a 30-lens. The imaging distance from the sample to the camera was 1 m.

Numerous modifications and variations of the present disclosure are possible in light of the above teachings. It is therefore to be understood that within the scope of the appended claims, the invention may be practiced otherwise than as specifically described herein.

The invention claimed is:

1. An upconversion phosphor, having the following formula:

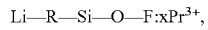

wherein R is Y or Lu, wherein x is 0.001 to 5 and represents mole percentage (%) based on the total number of moles of all elements in the upconversion phosphor, and wherein following excitation with sunlight the upconversion phosphor emits light having a wavelength in a range of 250 nanometers (nm) to 350 nm.

2. The upconversion phosphor of claim 1, wherein following excitation with sunlight the upconversion phosphor emits light having a maximum peak wavelength in a range of 255 nm to 270 nm.

3. The upconversion phosphor of claim 1, having a formula of (LiYSiO$_4$)(LiF)$_n$:xPr$^{3+}$, wherein n is 0.1 to 3.

4. The upconversion phosphor of claim 1, having a formula of (Y$_2$SiO$_5$)(LiF)$_n$:xPr$^{3+}$, wherein n is 0.1 to 3.

5. The upconversion phosphor of claim 1, having a formula of (LiLuSiO$_4$)(LiF)$_n$:xPr$^{3+}$, wherein n is 0.1 to 3.

6. The upconversion phosphor of claim 1, having a formula of (Lu$_2$SiO$_5$)(LiF)$_n$:xPr$^{3+}$, wherein n is 0.1 to 3.

7. The upconversion phosphor of claim 1, having a formula selected from the group consisting of LiYSiO$_{3.5}$F:xPr$^{3+}$, Li$_{1.6}$YSiO$_{3.5}$F$_{1.6}$:xPr$^{3+}$, Li$_{2.5}$YSiO$_4$F$_{1.5}$:xPr$^{3+}$, Li$_2$Y$_2$SiO$_5$F$_2$:xPr$^{3+}$, LiY$_2$Si$_{1.5}$O$_{4.5}$F$_4$:xPr$^{3+}$, Li$_{1.5}$Y$_2$SiO$_5$F$_{1.5}$:xPr$^{3+}$, and LiLu$_2$SiO$_5$F:xPr$^{3+}$.

8. The upconversion phosphor of claim 1, having at least one crystal phase selected from the group consisting of LiY$_3$(SiO$_4$)$_3$F$_2$ and β-Y$_2$Si$_2$O$_7$.

9. The upconversion phosphor of claim 1, wherein the upconversion phosphor does not comprise Pr$^{4+}$.

10. The upconversion phosphor of claim 1, having a powder particle size of 5 micrometers (μm) to 20 μm.

11. A paint, comprising:
the upconversion phosphor of claim 1; and
a fluoropolymer or silicone.

12. A method of upconverting light, comprising:
irradiating the upconversion phosphor of claim 1 with the light,
wherein upon the irradiating the upconversion phosphor converts the light to a shorter wavelength light.

13. The method of claim 12, wherein the light is from a broadband light source from 300 nm to 625 nm selected from a group consisting of natural sunlight, simulated sunlight, or a mix of LED light.

14. The method of claim 12, wherein the light has a power density of 0.1 milliwatt per square centimeter (mW/cm$^2$) to 1000 mW/cm$^2$.

15. The method of claim 12, wherein the shorter wavelength light has a wavelength in a range of 250 nm to 350 nm.

16. The method of claim 12, wherein the shorter wavelength light has a maximum peak wavelength in a range of 255 nm to 270 nm.

17. The method of claim 12, wherein the upconversion phosphor has a formula selected from the group consisting of LiYSiO$_{3.5}$F:xPr$^{3+}$, Li$_{1.6}$YSiO$_{3.5}$F$_{1.6}$:xPr$^{3+}$, Li$_{2.5}$YSiO$_4$F$_{1.5}$:xPr$^{3+}$, Li$_2$Y$_2$SiO$_5$F$_2$:xPr$^{3+}$, LiY$_2$Si$_{1.5}$O$_{4.5}$F$_4$:xPr$^{3+}$, Li$_{1.5}$Y$_2$SiO$_5$F$_{1.5}$:xPr$^{3+}$, and LiLu$_2$SiO$_5$F:xPr$^{3+}$.

18. The method of claim 12, wherein the upconversion phosphor is dispersed in water.

19. The method of claim 12, wherein the shorter wavelength light is capable of disinfecting a surface or a solution.

* * * * *